US010340040B2

(12) United States Patent
Loeb et al.

(10) Patent No.: US 10,340,040 B2
(45) **Date of Patent: *Jul. 2, 2019**

(54) METHOD AND SYSTEM FOR IDENTIFYING DIAGNOSTIC AND THERAPEUTIC OPTIONS FOR MEDICAL CONDITIONS USING ELECTRONIC HEALTH RECORDS

(71) Applicant: Biomed Concepts Inc., South Pasadena, CA (US)

(72) Inventors: Gerald E. Loeb, South Pasadena, CA (US); Jeremy A. Fishel, Fullerton, CA (US)

(73) Assignee: BIOMED CONCEPTS INC., South Pasadena, CA (US)

( * ) Notice: Subject to any disclaimer, the term of this patent is extended or adjusted under 35 U.S.C. 154(b) by 101 days.

This patent is subject to a terminal disclaimer.

(21) Appl. No.: 15/452,492

(22) Filed: Mar. 7, 2017

(65) Prior Publication Data

US 2017/0199987 A1 Jul. 13, 2017

Related U.S. Application Data

(63) Continuation of application No. 15/409,469, filed on Jan. 18, 2017, which is a continuation-in-part of
(Continued)

(51) Int. Cl.
*G06Q 50/00* (2012.01)
*G16H 10/60* (2018.01)
(Continued)

(52) U.S. Cl.
CPC .......... *G16H 10/60* (2018.01); *G06F 19/328* (2013.01); *G06F 19/3481* (2013.01);
(Continued)

(58) Field of Classification Search
CPC ........ G06Q 50/22; G06Q 50/24; G06Q 40/08; G06Q 10/10; G06F 19/322; G06F 17/30;
(Continued)

(56) References Cited

U.S. PATENT DOCUMENTS

| | | | |
|---|---|---|---|
| 2014/0195195 A1 | 7/2014 | Fishel et al. | |
| 2015/0205825 A1* | 7/2015 | Sengupta .......... | G06F 17/30312 707/758 |

FOREIGN PATENT DOCUMENTS

| | | | |
|---|---|---|---|
| WO | 2015055825 A1 | 4/2015 | |

OTHER PUBLICATIONS

International Search Report and Written Opinion issued in International Application No. PCT/US2017/013992, dated Apr. 4, 2017 (12 pages).

* cited by examiner

*Primary Examiner* — Tran N Nguyen
(74) *Attorney, Agent, or Firm* — Ferguson Braswell Fraser Kubasta PC

(57) ABSTRACT

A method for identifying diagnostic and therapeutic options for medical conditions. The method includes obtaining, from patient data in electronic health records, a diagnoses statistics database that includes statistical distributions of values of action results associated with diagnoses, and for each action result, a benefit of using the action result for disambiguating pairs of diagnoses. The method further includes obtaining an initial differential diagnosis for a patient. The initial differential diagnosis includes a set of initial diagnoses that are based on initially available patient data. Each initial diagnosis is assigned a probability that the initial diagnosis correctly identifies a condition of the patient. The method further includes identifying, based on the benefits of action results obtained for pairs of diagnoses, actions that have a largest benefit for disambiguation of the differential
(Continued)

diagnosis, and providing a subset of actions, selected from the actions, and associated benefits to a physician.

26 Claims, 14 Drawing Sheets

Related U.S. Application Data application No. 15/269,408, filed on Sep. 19, 2016, now Pat. No. 9,690,906, which is a continuation of application No. 14/151,625, filed on Jan. 9, 2014, now Pat. No. 9,477,909.

(60) Provisional application No. 62/280,172, filed on Jan. 19, 2016, provisional application No. 61/750,674, filed on Jan. 9, 2013.

(51) Int. Cl.

| | |
|---|---|
| ***G06F 19/00*** | (2018.01) |
| ***G16H 50/20*** | (2018.01) |
| ***G06K 9/62*** | (2006.01) |
| ***G16H 50/70*** | (2018.01) |
| *G06Q 10/00* | (2012.01) |

(52) U.S. Cl.

CPC .......... *G06K 9/6277* (2013.01); *G16H 50/20* (2018.01); *G16H 50/70* (2018.01)

(58) Field of Classification Search

CPC ........ G06F 19/30; G06F 19/32; G06F 19/321; G06F 19/324; G06F 19/325; G06F 19/326; G06F 19/328; G06F 19/34; G06F 19/3418; G06F 19/36; G06F 19/3456; G06F 19/3462; G06F 19/3468; G06F 19/3475; G06F 19/3481; A61N 1/08; G16H 10/10; G16H 10/20; G16H 10/40; G16H 10/60; G16H 10/65; G16H 15/00; G16H 20/00; G16H 20/10; G16H 20/13; G16H 20/17; G16H 20/30; G16H 20/40; G16H 20/60; G16H 20/70; G16H 20/90; G16H 30/00; G16H 30/20; G16H 30/40; G16H 40/00; G16H 40/20; G16H 40/40; G16H 40/60; G16H 40/63; G16H 40/67; G16H 50/00; G16H 50/20; G16H 50/30; G16H 50/50; G16H 50/70; G16H 50/80; G16H 70/00; G16H 70/20; G16H 70/14; G16H 70/60; G16H 80/00

See application file for complete search history.

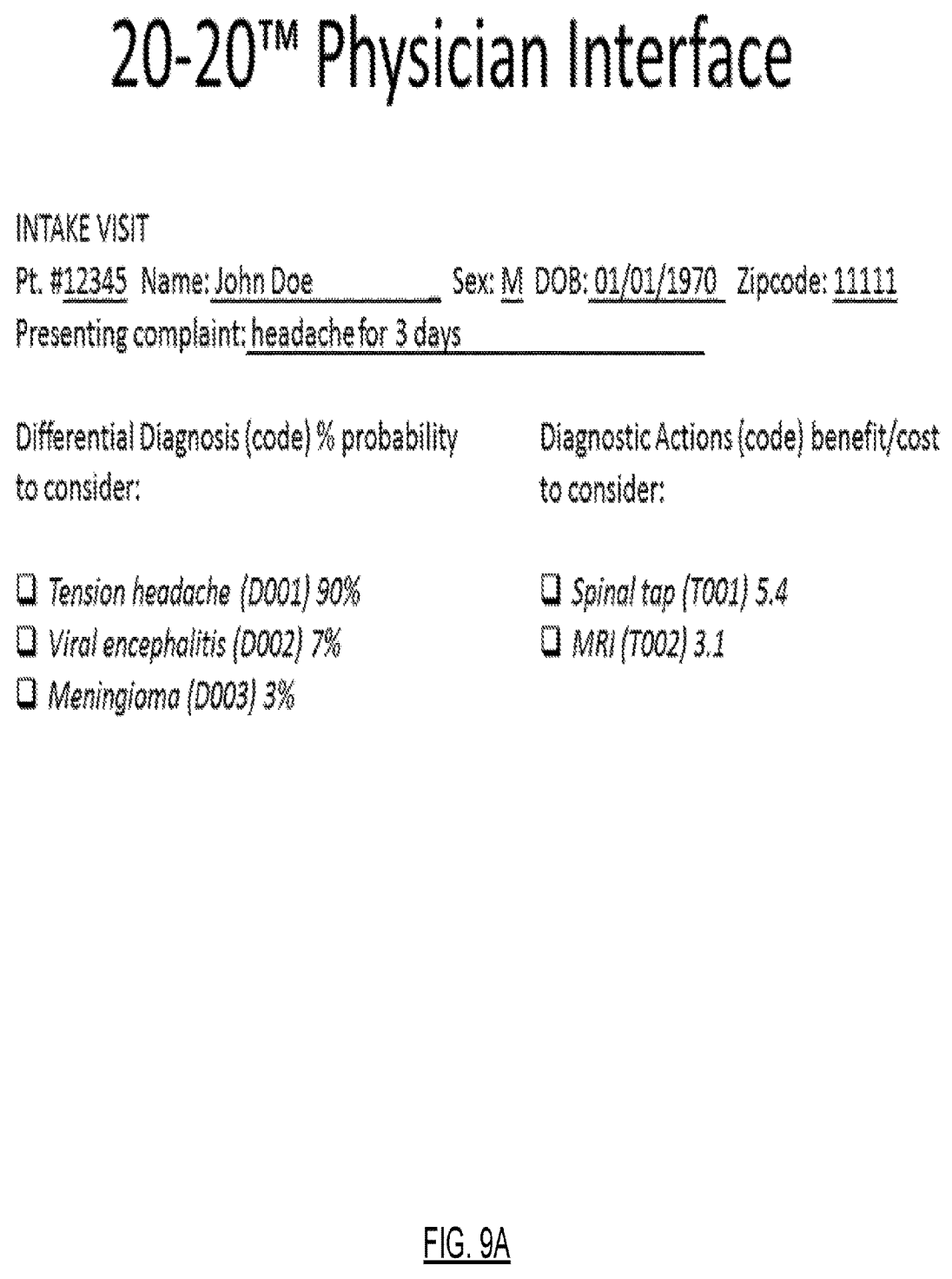

20-20™ Physician Interface

INTAKE VISIT

Pt. #12345 Name: John Doe Sex: M DOB: 01/01/1970 Zipcode: 11111

Presenting complaint: headache for 3 days

Differential Diagnosis (code) % probability to consider:

- ❑ *Tension headache (D001) 90%*
- ❑ *Viral encephalitis (D002) 7%*
- ❑ *Meningioma (D003) 3%*

Diagnostic Actions (code) benefit/cost to consider:

- ❑ *Spinal tap (T001) 5.4*
- ❑ *MRI (T002) 3.1*

FIG. 9A

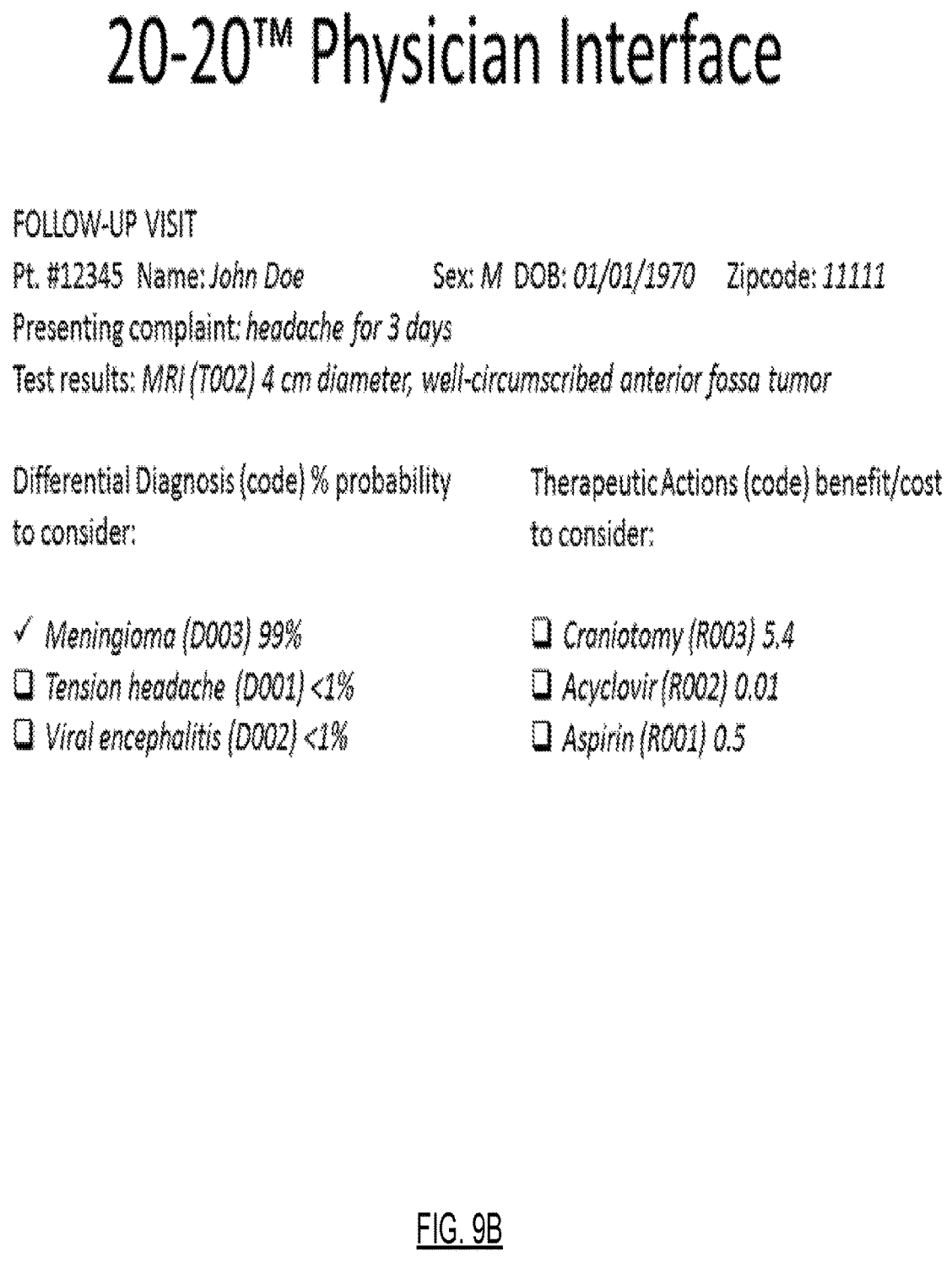

20-20™ Physician Interface

FOLLOW-UP VISIT

Pt. #12345 Name: *John Doe* Sex: *M* DOB: *01/01/1970* Zipcode: *11111*

Presenting complaint: *headache for 3 days*

Test results: *MRI (T002) 4 cm diameter, well-circumscribed anterior fossa tumor*

Differential Diagnosis (code) % probability to consider:

- ✓ *Meningioma (D003) 99%*
- ❑ *Tension headache (D001) <1%*
- ❑ *Viral encephalitis (D002) <1%*

Therapeutic Actions (code) benefit/cost to consider:

- ❑ *Craniotomy (R003) 5.4*
- ❑ *Acyclovir (R002) 0.01*
- ❑ *Aspirin (R001) 0.5*

FIG. 9B

20-20™ Consumer Interface

Name: John Doe Sex: M DOB: 01/01/1970 Zipcode: 11111
Health problem: headache for 3 days

| Possibilities to consider: | Tests you might need: | Sponsored Ads: |
| --- | --- | --- |
| ❑ *Tension headache (code: D001)* | ❑ *Spinal tap (code: T001)* | |
| ❑ *Viral encephalitis (code: D002)* | ❑ *MRI (code: T002)* | *Body Imaging Services Inc.* |
| ❑ *Meningioma (code: D003)* | | |

FIG. 9C

20-20™ Epidemiologist Interface

SEARCH CRITERIA

| Codes: | Zipcodes: | Anomaly size (s.d.): | Timeframe (mm/yyyy): |
|---|---|---|---|
| D(all) | all | >2.0 | 01/2010-12/2016 |

RESULTS

| Codes: | Zipcodes: | Anomaly size (s.d.): |
|---|---|---|
| *D003* | *11111* | *3.0* |

FIG. 9D

METHOD AND SYSTEM FOR IDENTIFYING DIAGNOSTIC AND THERAPEUTIC OPTIONS FOR MEDICAL CONDITIONS USING ELECTRONIC HEALTH RECORDS

CROSS-REFERENCE TO RELATED APPLICATIONS

This application claims priority to U.S. Provisional Patent Application No. 62/280,172 filed Jan. 19, 2016, the entire disclosure of which is hereby expressly incorporated by reference herein. This application further claims priority to U.S. patent application Ser. No. 15/269,408 filed Sep. 19, 2016, which is a continuation of U.S. Pat. No. 9,477,909, issued Oct. 25, 2016, the entire disclosure of which is hereby expressly incorporated by reference herein.

BACKGROUND

Patients usually present themselves to physicians with a problem that they wish to understand and mitigate. This problem is usually identified as a “chief complaint”. The physician uses the process of “diagnosis” to identify the cause of the problem, which will generally be associated with various options for treatment. The diagnostic process generally requires the serial collection of information from at least one or more processes that are well known to the practice of medicine.

SUMMARY

In general, in one aspect, the invention relates to a non-transitory computer medium comprising instructions, that enable a system for identifying diagnostic and therapeutic options for medical conditions using electronic health records to obtain, from a plurality of electronic health records of patients, diagnoses of the patients and values of action results associated with the diagnoses. The instructions further enable the system to generate, for the diagnoses, statistical distributions of the values of the action results, determine, for a plurality of pairs of diagnoses, and separately for different action results, an overlap of the statistical distributions, obtain, for each pair of diagnoses, based on the overlap of the associated statistical distributions, a benefit of using the associated action result for disambiguating the pair of diagnoses, and obtain an initial differential diagnosis for a patient with an undiagnosed condition. The initial differential diagnosis comprises a plurality of initial diagnoses that are based on initially available patient data, and each initial diagnosis of the plurality of initial diagnoses is assigned a probability that the initial diagnosis correctly identifies the condition of the patient. The instructions further enable the system to identify, based on the benefits of action results obtained for pairs of diagnoses, a plurality of actions that have a largest benefit for disambiguation of the differential diagnosis; and provide a subset of actions, selected from the plurality of actions, and associated benefits to a physician.

In general, in one aspect, the invention relates to a method for identifying diagnostic and therapeutic options for medical conditions using electronic health records. The method comprises obtaining, from a plurality of electronic health records of patients, diagnoses of the patients, and values of action results associated with the diagnoses. The method further comprises generating, for the diagnoses, statistical distributions of the values of the action results, determining, for a plurality of pairs of diagnoses, and separately for different action results, an overlap of the statistical distributions, and obtaining, for each pair of diagnoses, based on the overlap of the associated statistical distributions, a benefit of using the associated action result for disambiguating the pair of diagnoses. The method further comprises obtaining an initial differential diagnosis for a patient with an undiagnosed condition, wherein the initial differential diagnosis comprises a plurality of initial diagnoses that are based on initially available patient data, and wherein each initial diagnosis of the plurality of initial diagnoses is assigned a probability that the initial diagnosis correctly identifies the condition of the patient. In addition, the method comprises identifying, based on the benefits of action results obtained for pairs of diagnoses, a plurality of actions that have a largest benefit for disambiguation of the differential diagnosis, and providing a subset of actions, selected from the plurality of actions, and associated benefits to a physician.

BRIEF DESCRIPTION OF DRAWINGS

FIGS. 9A-9D show exemplary user interfaces, in accordance with one or more embodiments of the invention.

DETAILED DESCRIPTION

Figure 1A:
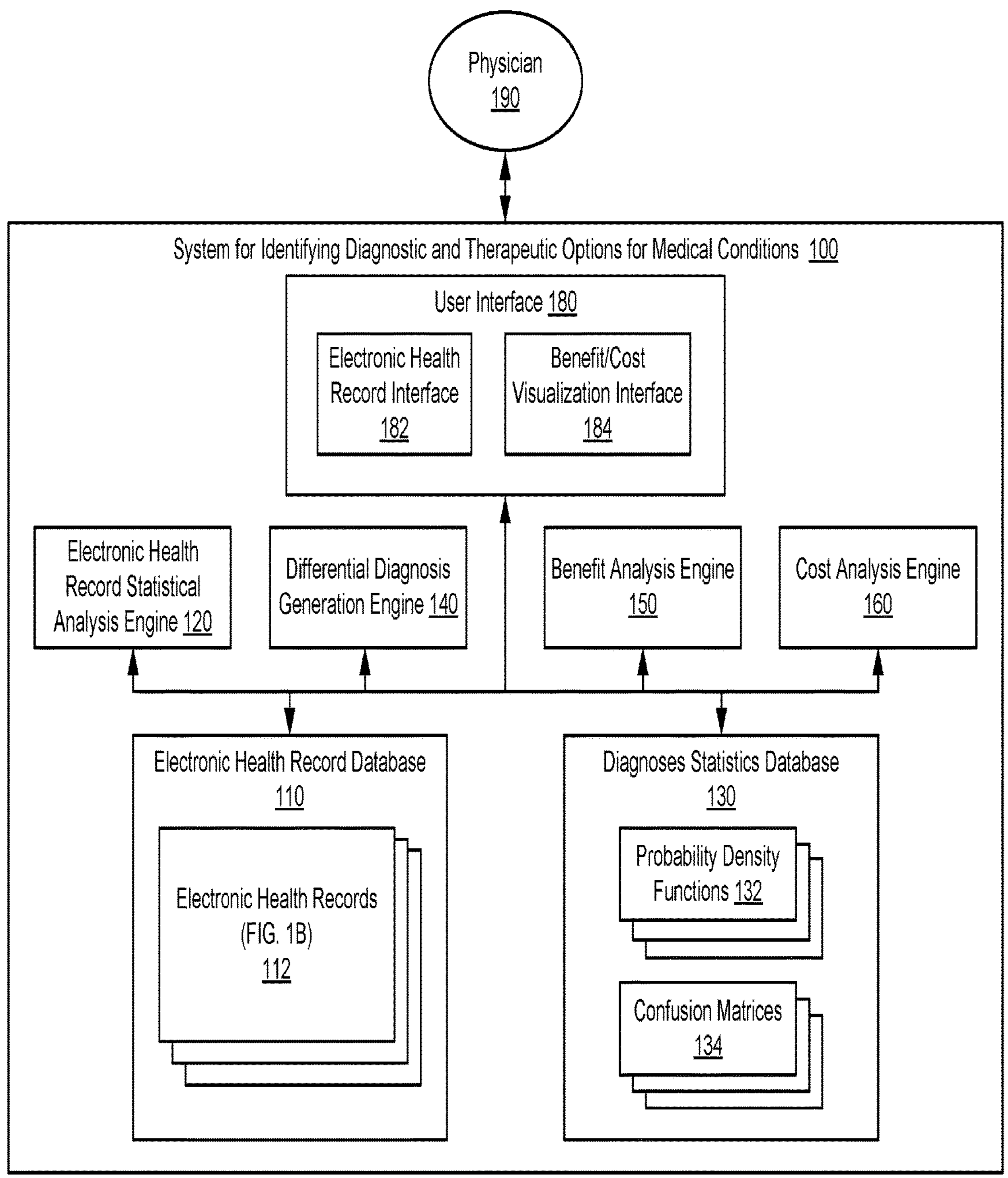
FIG. 1A shows a system for identifying diagnostic and therapeutic options for medical conditions, in accordance with one or more embodiments of the invention.

Specific embodiments of the invention will now be described in detail with reference to the accompanying figures. In the following detailed description of embodiments of the invention, numerous specific details are set forth in order to provide a more thorough understanding of the invention. However, it will be apparent to one of ordinary skill in the art that the invention may be practiced without these specific details. In other instances, well-known features have not been described in detail to avoid unnecessarily complicating the description.

In the following description of FIGS. 1A-10, any component described with regard to a figure, in various embodiments of the invention, may be equivalent to one or more like-named components described with regard to any other figure. For brevity, descriptions of these components will not be repeated with regard to each figure. Thus, each and every embodiment of the components of each figure is incorporated by reference and assumed to be optionally present within every other figure having one or more like-named components. Additionally, in accordance with various embodiments of the invention, any description of the components of a figure is to be interpreted as an optional embodiment, which may be implemented in addition to, in conjunction with, or in place of the embodiments described with regard to a corresponding like-named component in any other figure.

In general, embodiments of the invention relate to the field of diagnosis and treatment of medical conditions. More specifically, embodiments of the invention relate to a method and a system for identifying diagnostic and therapeutic options for medical conditions, using electronic health records. Methods in accordance with one or more embodiments of the invention include the preparation and compilation of a statistical database from individual electronic health records that may contain formally defined identification terms for various clinical diagnoses, various diagnostic and therapeutic procedures, and the results of those procedures as reported for a large number of patients. The methods in accordance with one or more embodiments of the invention further include the iterative, quantitative evaluation of the anticipated efficacy of alternative diagnostic, preventive and/or therapeutic procedures. These evaluations may consider the prior information already available about the patient and his or her medical condition(s) as well as the costs of the alternative procedures, where costs may consider factors including financial expense, temporal delay and/or risk of adverse events. In combination, above described methods enable the identification of a set of clinical actions that are deemed particularly beneficial for a patient seen by the physician. The physician may review these suggested clinical actions to determine a course of action for diagnosing and/or treating the patient. A system capable of implementing these functionalities is subsequently described with reference to FIGS. 1A and 1B. The use of the system, by a physician is then illustrated in FIG. 2. Various methods in accordance with one or more embodiments of the invention, executed by the system are described with reference to FIGS. 3-7.

FIG. 1A shows a system for identifying diagnostic and therapeutic options for medical conditions (100), in accordance with one or more embodiments of the invention. In one embodiment of the invention, the system (100) includes an electronic health record database (110), an electronic health record statistical analysis engine (120), a diagnoses statistics database (130), a differential diagnosis generation engine (140), a benefit analysis engine (150), a cost analysis engine (160) and a user interface (180). The system (100) may be operated by a physician (190). Each of these components is subsequently described.

Turning to FIG. 1A, the electronic health record database (110) includes electronic health records for large numbers of patients. One electronic health record (112) may exist for each patient or each encounter with a patient. A description of the content of an electronic health record (112) is provided below, with reference to FIG. 1B. The electronic health records database (110), in accordance with an embodiment of the invention, thus provides sufficient depth and breadth of information to capture what actually happens to large numbers of patients in medical practice. Formal coding systems may be relied upon to give each diagnosis and/or procedure in an electronic health record (112) a unique and machine-searchable identifier so that individual electronic health records can be combined into a large database that can be processed by computerized software algorithms. Embodiments of the invention, may rely on the content of the electronic health records database (110) to identify the best options for each individual patient based on whatever information is currently available for that specific patient as further described below with reference to FIGS. 3-7. Various filters, cleaners, translators, synonyms, statistical analyses and other computerized methods for individual and/or institutional records may be used in order to create, maintain and/or access the electronic health record database (110).

Figure 1B:
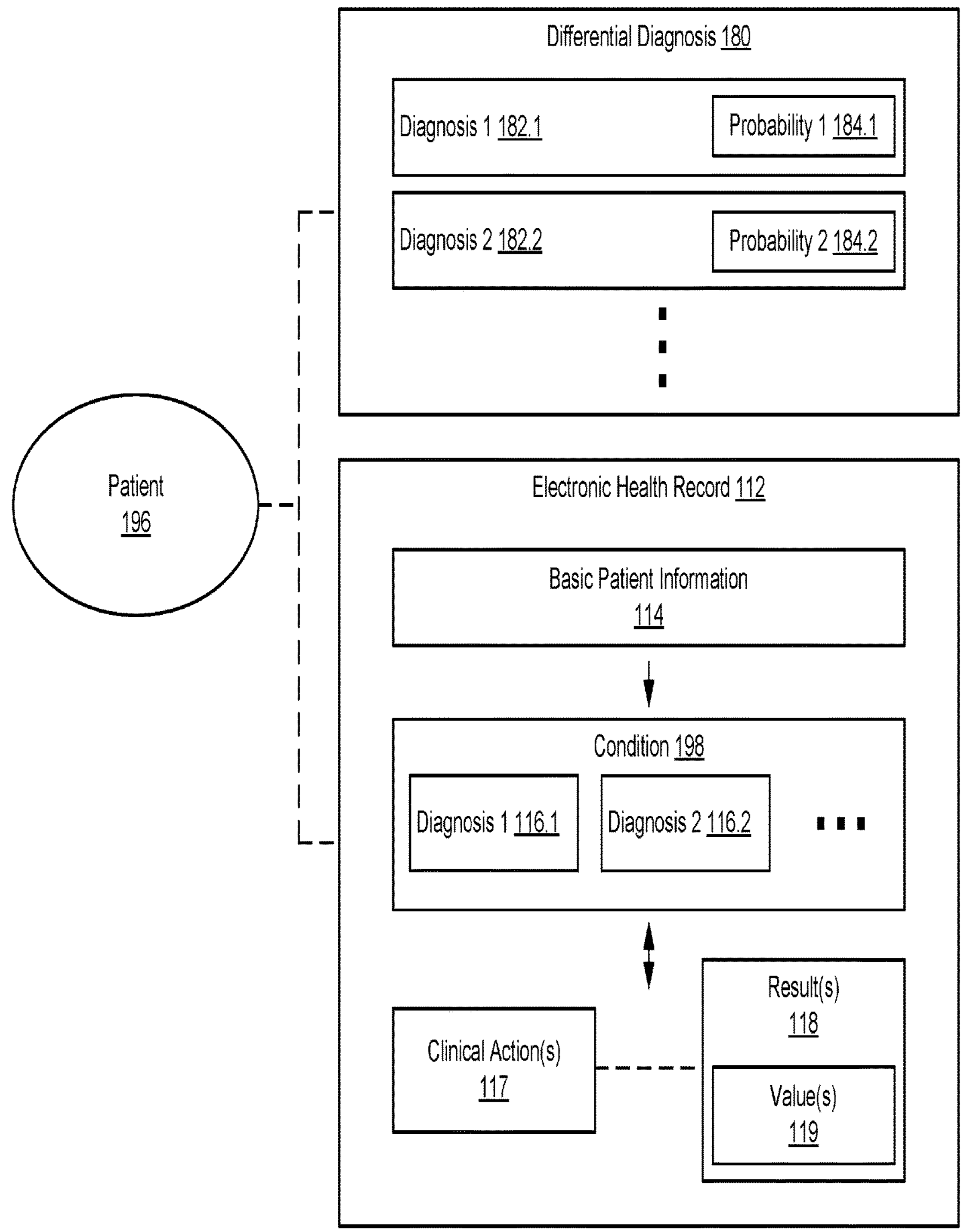
FIG. 1B shows an electronic health record and a differential diagnosis, associated with a patient, in accordance with one or more embodiments of the invention.

The electronic health record database (110) used for the storage of electronic health records (112) may be implemented using any format suitable for the storage of electronic health record content as described in FIG. 1B. The database may be, for example, any type of hierarchical, relational and/or object oriented collection of data. The electronic health record database (110) may be hosted in non-volatile memory, e.g., on a hard disk drive, a redundant array of independent disks (RAID), network attached storage (NAS), cloud storage, etc. Further, at least some of the content of the electronic health record database (110) may alternatively or in addition be stored in volatile memory, e.g., Dynamic Random-Access Memory (DRAM), Synchronous DRAM, SDR SDRAM, and DDR SDRAM. Those skilled in the art will recognize that the electronic health record database (110) may be under the administration of various legal entities such as healthcare providers, health insurance providers, government agencies, etc.

The system (100) further includes an electronic health record statistical analysis engine (120), in accordance with an embodiment of the invention. The electronic health record statistical analysis engine (120), in accordance with one or more embodiments of the invention, performs statistical processing of the electronic health records (112) that are stored in the electronic health record database (110). The information obtained from the processing is stored in the diagnoses statistics database (130). To perform the statistical processing, the electronic health record statistical analysis engine (120) executes software instructions in the form of non-transitory computer readable program code described in detail below, with reference to FIGS. 3 and 4. The statistical processing of the electronic health records, performed by the health record statistical analysis engine (120), in accordance with an embodiment of the invention, facilitates the execution of other steps of the method, as further described below. Specifically, the health record statistical analysis engine (120) may perform the potentially time-consuming statistical processing of large numbers of electronic health records (112) offline, while other steps of the method may be performed online. The results of the offline statistical processing, stored in the diagnoses statistics database, thus enable a timely response of the system (100) to a query submitted by a physician (190).

Continuing with the discussion of FIG. 1A, the system (100) further includes a diagnoses statistics database (130). As previously described, the diagnoses statistics database (130) is generated and/or updated by the electronic health record statistical analysis engine (120) performing the at least some of the steps shown in FIGS. 3 and 4. The diagnoses statistics database (130) may include probability density functions (132) and/or confusion matrices (134).

The probability density functions (132), in accordance with an embodiment of the invention, describe the distribution of result values obtained for a particular action, given a particular condition of the patient. Consider, for example a patient complaining of a cold. The physician may diagnose the cold using certain clinical actions such as diagnostic tests. Based on these clinical actions, the physician may conclude that the diagnosed condition of the patient is the medical term for a cold—viral upper respiratory syndrome. One such diagnostic action may be the measuring of the patient's body temperature. The result of the action may be a temperature, and, the temperature value may be, for example 40° C., indicating that the patient has a fever. The electronic health record statistical analysis engine (120) may search multiple (or many, or all) electronic health records (112) for the diagnosed condition "viral upper respiratory syndrome". In some of these health records, associated with various patients, the patients' physicians may have recorded and reported the body temperature. A distribution of body temperature values may thus be obtained for the diagnosed condition "viral upper respiratory syndrome". This distribution may be a statistically normal distribution that may be characterized by a mean and standard deviation, or any distribution that may be described by a probability density function. Further, other probability density functions may be obtained for the same diagnosed condition but for different results obtained from different actions. For example, physicians may also visually assess the redness of the throat to determine whether a patient has a viral upper respiratory syndrome. Accordingly, a separate probability density function may be obtained for the diagnosed condition "viral upper respiratory syndrome", based on throat redness values observed by the physicians. In addition, probability density functions may be obtained for other conditions, such as for the diagnosed condition "strep throat". The same or different actions may be used by the physician to diagnose the condition. In case of the condition "strep throat", the physician may also measure body temperature and assess throat redness. Accordingly, an additional probability density function may exist for the diagnosed condition "strep throat", formed by body temperature values, and yet another probability density function may exist for the diagnosed condition "strep throat", formed by throat redness values. Those skilled in the art will appreciate that the diagnoses statistics database may include many probability density functions for many diagnosed conditions, based on many measurement results, and may solely be limited by the content of the electronic health records (112). In one embodiment of the invention, the probability density distributions, may be relied upon, in order to probabilistically assess the usefulness of a clinical action for disambiguating diagnoses. More specifically, the degree of overlap of the probability density functions obtained based on the same results associated with a particular clinical action, but for different diagnosed conditions may indicate the degree of benefit of that particular clinical action for disambiguating these diagnoses. Consider, the above-introduced examples of the two diagnoses "viral upper respiratory syndrome" and "strep throat", and assume that the probability density functions associated with the result "body temperature" mostly overlap for these two diagnoses. This overlap suggests that taking a patient's body temperature may not be a useful diagnostic action for disambiguating the diagnoses "viral upper respiratory syndrome" and "strep throat". In addition, assume that the probability density functions associated with the result "throat redness" barely overlap for these two diagnoses. This lack of overlap suggests that examining the patient's throat may be a useful diagnostic action for disambiguating the diagnoses "cold" and "strep throat". The result of that diagnostic action might motivate an additional action such as obtaining a throat culture. The iterative nature of this process is discussed below with reference to FIGS. 2 and 5.

The confusion matrices (134), in accordance with an embodiment of the invention, may be used to form a compact and accessible representation of the overlap between probability density functions obtained for diagnosed conditions. A separate confusion matrix may be stablished for each result of an action. For this result of the action, the confusion matrix indicates the benefit of using this particular result of the action for disambiguating any of the diagnoses for which probability density functions were established, in accordance with an embodiment of the invention. A description of the generation and use of confusion matrices is described below with reference to FIGS. 4 and 6.

The diagnoses statistics database (130) thus includes a statistics-based summary of the usefulness of clinical actions for disambiguating a set of potential diagnoses of a patient being examined, that is based on the content of electronic health records of patients that were previously seen by physicians. The diagnoses statistics database may be implemented in any format that allows the storage of numerous probability density functions and/or confusion matrices. The diagnoses statistics database (130) may be hosted in non-volatile memory, e.g., on a hard disk drive, a redundant array of independent disks (RAID), network attached storage (NAS), cloud storage, etc. Further, at least some of the content of the diagnoses statistics database (130) may alternatively or in addition be stored in volatile memory, e.g., Dynamic Random-Access Memory (DRAM), Synchronous DRAM, SDR SDRAM, and DDR SDRAM.

Continuing with the discussion of FIG. 1A, the system (100) further includes a differential diagnosis generation engine (140), in accordance with an embodiment of the invention. The differential diagnosis generation engine (140), in accordance with one or more embodiments of the invention, establishes a differential diagnosis for the patient being seen by the physician (190). The differential diagnosis, in accordance with an embodiment of the invention, includes a set of diagnoses with associated probabilities that they would be judged to be a condition of the patient according to the current standard of practice of medicine. These probabilities would be computed from the electronic health record database (110) by Bayesian inference based on initial information available about the patient including data collected from the patient and/or the patient's electronic health record. A detailed description of the differential diagnosis is provided below, with reference to FIG. 1B. To obtain the differential diagnosis, the differential diagnosis generation engine (140) executes software instructions in the form of non-transitory computer readable program code described in detail below, with reference to FIG. 5.

In one embodiment of the invention, the system (100) also includes a benefit analysis engine (150). The benefit analysis engine (150), in accordance with one or more embodiments of the invention, identifies clinical actions that have a largest benefit for the disambiguation of the differential diagnosis, based on information obtained from the diagnoses statistics database (130), or directly from the electronic health records database (110). To perform the disambiguation, the differential diagnosis generation engine (140) executes software instructions in the form of non-transitory computer readable program code described in detail below, with reference to FIG. 6.

The system (100) further includes a cost analysis engine (160), in accordance with an embodiment of the invention. The cost analysis engine (160), in accordance with one or more embodiments of the invention, obtains the cost associated with selected actions. The actions for which a cost is calculated may be selected from the actions previously identified by the benefit analysis engine. Various costs beyond financial costs may be considered. To perform the cost calculation, the cost analysis engine (160) executes software instructions in the form of non-transitory computer readable program code described in detail below, with reference to FIG. 7.

The system (100) also includes a user interface (180). While the user interface provides a general interface for the physician (190) to interact with the various element of the system (100), the design of aspects of the user interface may be specific to particular applications. In one embodiment of the invention, the user interface (180) facilitates the efficient addition of information to the patient's electronic health record by presenting the physician with lists of the most relevant potential diagnoses and most useful actions for diagnosis and/or treatment, and by providing means for the physician to select one or more of the presented diagnoses and/or actions. A variety of exemplary user interfaces are described below, with reference to FIGS. 9A-9D.

Generally, the user interface may include a GUI that displays information on a display device, such as a computer monitor or a touchscreen on a handheld computer device. The GUI may include various GUI tools that organize what data is shown as well as how data is presented to a user. Furthermore, the GUI may present data directly to the physician, e.g., data presented as actual data values through text, or rendered by the computing device into a visual representation of the data, such as through visualizing a data model. The GUI may further be used to enable a physician to submit data. Data may be submitted via the GUI by the physician selecting one or more graphical user interface tools or inserting text and other data into graphical user interface tools using a touch screen, a touchpad, a keyboard, a mouse, or any other input device.

In one embodiment of the invention, the user interface includes an electronic health record interface (182) and/or a benefit vs. cost visualization interface (184).

The electronic health record interface (182) may be relied upon by the physician (190) for activities that require access of one or more electronic health records (112) in the electronic health record database (110). The activities include, but are not limited to, the retrieval of the electronic health record of the patient currently being seen by the physician and the entering of new information (e.g. a diagnosis, results of an observation or other action, general patient information, etc.).

The benefit vs. cost visualization interface (184) may be relied upon by the physician (190) to obtain information regarding clinical actions and their associated costs, obtained as described below with reference to FIGS. 3-7. The benefit vs cost visualization interface (184) may include control elements that enable the physician (190) to manipulate the displayed content. For example, controls may exist to display results in a particular order, e.g., sorted by cost and/or by benefit, to apply filters to enabling the physician to eliminate certain results, to perform a search for a particular result, etc.

One skilled in the art will recognize that the architecture of the system (100) is not limited to the components shown in FIG. 1A. For example, the system (100) or even components of the system, such as the electronic health record database (110), may be distributed. In case of a distributed system, components of the system may communicate using any combination of wired and/or wireless communication protocols. In one embodiment of the invention, at least some of the components of the system communicate via a wide area network (e.g., over the Internet), and/or a local area network (e.g., an enterprise or home network). The communication between the components of the system (100) may include any combination of secured (e.g., encrypted) and non-secured (e.g., non-encrypted) communications. The manner in which the components of the system (100) communicate may vary based on the implementation of the invention. Finally, while the system (100) includes various engines (120, 140, 150 and 160), those skilled in the art will appreciate that the operations performed by these engines may be distributed in different ways, without departing from the invention.

FIG. 1B shows an electronic health record and a differential diagnosis, associated with a patient, in accordance with one or more embodiments of the invention.

In one embodiment of the invention the electronic health record (112) is specific to a particular patient (196) and includes basic patient information (114) such as sex, age and address, plus all diagnoses (116) that have previously been ascribed to be a condition (198) of the patient, plus all previously performed clinical actions (117) and the values (119) of the results (118) thereby obtained.

FIG. 1B depicts the situation of Patient (196) at a given point in time such as at a health care encounter motivated by the occurrence of a new symptom or other concern of the patient. This motivating event typically may be added to the electronic health record as a chief complaint, which is a result of the action of the scheduling or intake process for the encounter. It is also possible that the motivating event for the encounter is simply a normal check-up, in which case the electronic health record will likely now include the results of the actions associated with such an encounter, including taking vital signs such as blood pressure. System (100) may now apply differential diagnosis generation engine (140) as described with reference to FIG. 1A, in order to generate a differential diagnosis (180) as depicted in FIG. 1B. It is also possible that the motivating event for the current encounter is to follow up on a previous encounter in which a differential diagnosis (180) was obtained but the physician has not yet accepted any of the diagnoses on the list to be a condition of the patient. The physician (190) may interact with the patient (196) so as to receive additional results of those actions that may change the probabilities (184.*n*) of the various diagnoses (182.*n*) being a condition (198) of the patient according to the standard of care reflected in the electronic health record database (110).

The electronic health record (112), associated with the patient (196) may include various patient-specific content such as basic patient information (114), a diagnosis (or multiple diagnoses) previously ascribed to be condition(s) (198) of the patient, clinical actions (117) and results (118) of these actions, expressed as result values (119). Each of these elements is subsequently described. The amount of information in the electronic health record may vary and may depend, for example, on the duration of the physician-patient relationship, the meticulousness with which information was (or was not) entered in the electronic health record, whether affiliated physicians or hospitals or commercial test services contribute information, etc. An electronic health record may thus be of any degree of completeness and accuracy, without departing from the invention.

Turning to the electronic health record (112), the basic patient information (114) may include, but is not limited to basic demographical information such as the patient's age, sex, race, etc. To obtain a reasonable amount of basic patient information, the physician may ask the patient or a caregiver questions regarding the onset and progression of the chief complaint, other symptoms that may be present, previous illnesses, injuries and medical procedures, pharmacologically active substances that the patient may be taking, similar problems that may have occurred to blood relatives, and socioeconomic and lifestyle factors that may be relevant. Some or all of the responses provided by the patient or the caregiver may be entered in the electronic health record (112) as basic patient information (114) or as results (118) of actions (117) of soliciting the responses, without departing from the invention.

The electronic health record may further include one or more diagnoses (116) indicative of any condition(s) (198) that a physician has already ascribed to the patient. The diagnoses that are listed as conditions of the patient or are being entertained as part of the differential diagnosis may be encoded in the electronic health record (112) based on coded lists for reimbursement or other purposes such as the International Classification of Diseases (ICD), including ICD-9 or ICD-10. A diagnosis, in accordance with an embodiment of the invention, may further include expectations of treatment and/or preventive outcomes, such as "successfully treated infection" or "recurrent carcinoma" or "well-patient".

The electronic health record may further include one or more clinical actions (117). An action may include any possible interactions of the physician with the patient, including but not limited to asking a question, performing a test, making an observation, ordering a diagnostic test or prescribing and/or administering a specific treatment or preventive measure. The following list provides a non-limiting set of exemplary actions that may be performed on a patient:

- Physical examination—Exploration and observation of the patient's body, typically including auscultation, palpation, manipulation, probing and results of sensory and motor tasks performed by the patient.
- Laboratory tests—Chemical, microscopic and microbiological analyses of readily obtained specimens such as blood, urine, saliva, sputum, feces, etc. These may be processed on-site or sent to diagnostic laboratories.
- Medical imaging—Use of specialized equipment to obtain planar or 3D representations of the physical tissues of the body such as by x-ray, computed tomography (CT), magnetic resonance imaging (MRI), ultrasound (US), positron emission tomography (PET), impedance tomography, radioisotope imaging, etc. These usually require sending the patient to an imaging machine.
- Electrophysiology—Use of specialized instruments to measure electrical signals associated with physiological functions such as electrocardiography (ECG), electroencephalography (EEG), electromyography (EMG), etc. These usually require sending the patient to the instrumentation.
- Functional tests—Various physiological functions can be assessed by making various specialized measurements while the patient performs a specific task such as rapid walking, deep breathing, micturition, etc. These usually require sending the patient to a specialized laboratory.
- Therapeutic trial—One common way to identify the cause of a problem is to assume one of the possible causes and initiate treatment that would resolve or mitigate that cause. This is particularly useful when one cause is highly likely and/or when prompt treatment of one cause is particularly important and/or when the costs and risks of such treatment are low compared to the diagnostic procedures required to achieve a definitive diagnosis before treatment.

The electronic health record may further include one or more results (118), obtained from performing an action (117). One or more results (118) may arise from a given action (117). For example, taking a patient's temperature yields one result but taking a patient's blood pressure yields two results (systolic and diastolic pressure). Results may be in numerical or Boolean form and may be derived from objective data from a diagnostic test or response of the patient or a caregiver to a posed question, or conclusory abstractions from a diagnostic test or from the observations of the patient or a caregiver, or conclusory abstractions extracted by an artificial intelligence system operating on complex data such as images derived from histological samples or imaging devices such as X-ray, fluoroscopy, CT, ultrasound, nuclear medicine and MRI machines.

In one embodiment of the invention, results of quantitative tests are expressed as values (119). Values may be normalized according to both the mean and the variance of the data generated by the action of performing a quantitative diagnostic test in healthy, comparable individuals, as described below.

The condition (198) of the patient (196) may ultimately include one of the diagnoses (182.*n*) in the differential diagnosis (180), based on actions having been performed on the patient and the associated results. A condition may be considered to be diagnosed automatically when the diagnosis' probability exceeds some conclusion threshold value, $P_{conclusion}$ or when the physician designates this as a condition of the patient for any reason.

In one embodiment of the invention, the electronic health record (112) includes also the diagnoses that were included in any differential diagnosis (180) that was available at the time that each clinical action (117) was undertaken and results (118) thereof were obtained. Electronic health record (112) may then be advantageously structured to be an associative database. Accordingly, querying the electronic health record for a diagnosis, an action or a result may return all the other terms associated with it. For example, querying the electronic health record for a given condition plus action would return information about the results associated with such a pair; querying the electronic health record for a condition plus a result would return the action associated with such a pair; and a given value of a result plus an action would return the likelihood that it is consistent with each condition. In one or more embodiments of the invention, such queries may be submitted to the health record database (110) to obtain a response for multiple or all of the electronic health records (112) stored in the health record database (110)

Continuing with the discussion of FIG. 1B. a differential diagnosis (180) is associated with the patient (196), in accordance with an embodiment of the invention. In one embodiment of the invention, the differential diagnosis (180) is the subset of diagnoses (182) and their probabilities (184) that they would be considered to be a condition (198) of the patient according to the standard of care reflected in the electronic health record database (110). Individual conditions that may give rise to interactions among results when said conditions are present simultaneously in a given patient may be identified as distinct items in diagnoses (182), such as "hepatorenal syndrome" or "toxic shock syndrome". Further, in one embodiment of the invention, diagnoses include expectations of treatment outcomes, such as "successfully treated infection" or "recurrent carcinoma".

Many items in diagnoses may have a vanishingly small probability of being a condition of a given patient, thus, the differential diagnosis may be delimited by some consideration threshold value, $P_{consideration}$, below which diagnoses are excluded from consideration.

Figure 2:
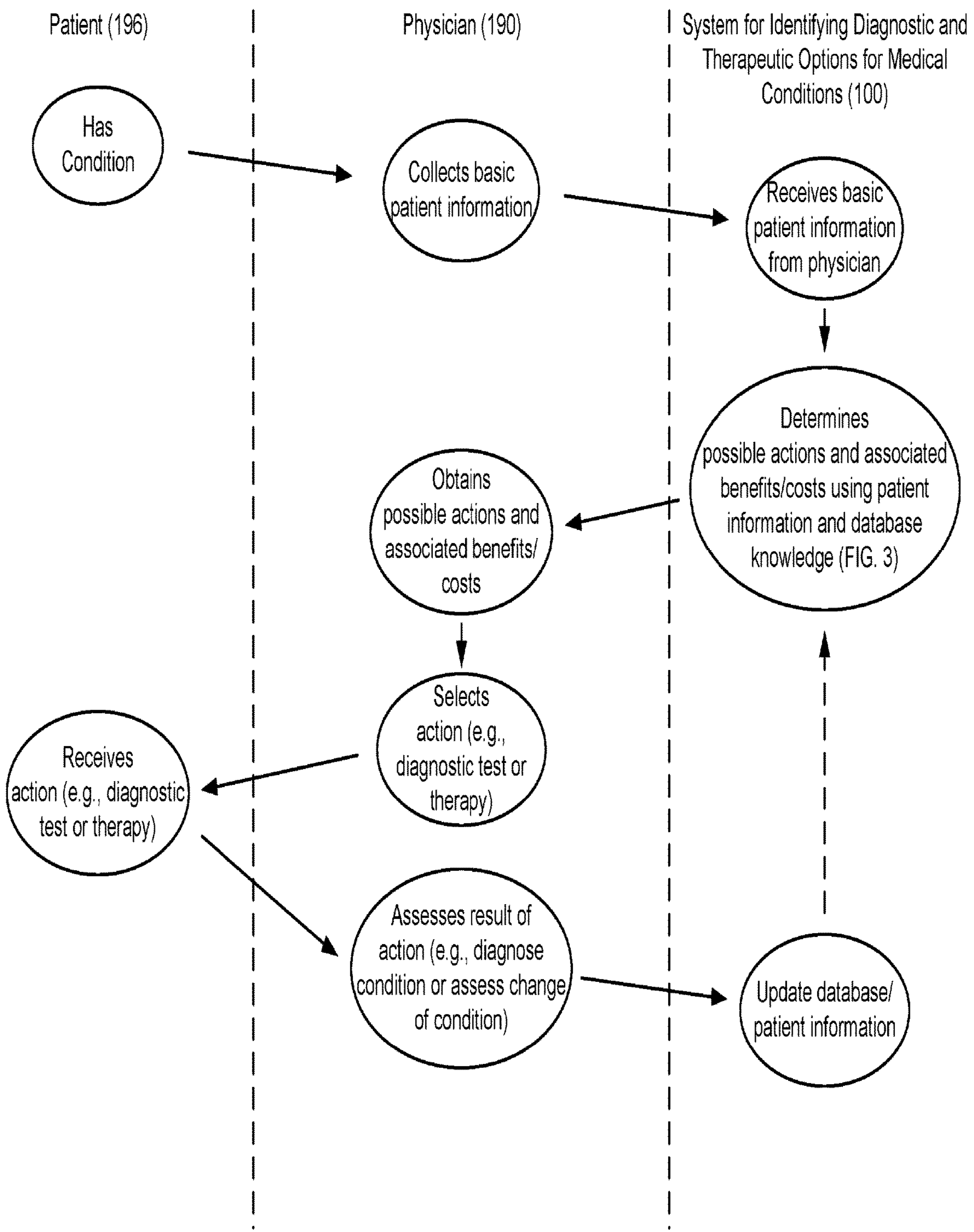
FIG. 2 shows an exemplary interaction between a patient, a physician and a system for identifying diagnostic and therapeutic options for medical conditions, in accordance with one or more embodiments of the invention.

FIG. 2 shows an exemplary interaction between a patient (196), a physician (190) and a system for identifying diagnostic and therapeutic options for medical conditions (100), in accordance with one or more embodiments of the invention.

Turning to FIG. 2, a patient with a potentially unknown condition visits a physician to have a condition diagnosed and/or to have a previously diagnosed condition treated. The physician collects basic patient information, as previously described and enters the collected information into the patient's electronic health record.

Subsequently, in accordance with one or more embodiments of the invention, the system determines possible actions and associated benefits and costs, based on the information available about the patient and based on statistical data obtained from the diagnoses statistics database. Actions determined by the system may be any kind of clinical actions, including any kind of diagnostic and therapeutic actions. These possible actions are provided to the physician. An extensive description of the steps performed by the system to determine a set of possible actions is subsequently provided with reference to FIGS. 3-7.

The physician reviews the received set of possible actions, their benefits and costs. Based on this review, the physician may select an action to be performed on the patient. It may be up to the physician to select the action to be performed. The physician may, for example, merely consider the provided set of possible actions as an advisory input that facilitates his/her selection of the action to be performed on the patient. Accordingly, the action to be performed may be any action selected from the set of the proposed actions, or it may even be an action that is not included in the set of proposed actions. In this scenario, the information provided by the system in the form of possible actions is purely informative or advisory. Alternatively, the physician may rely on the set of possible actions by selecting the proposed action with the highest benefit or with the highest benefit vs. cost ratio.

Based on the physician's selection of an action, the patient subsequently receives the action. If more than one diagnosis or action is under consideration, it may be advantageous for the physician to consider them simultaneously so as to identify opportunities for efficient use of time and resources. As is described in greater detail below, the actions that might be undertaken may include not just diagnostic tests but also therapeutic and preventive measures. In this case, the set of diagnoses to be considered may include states such as "cured disease" or "disease in remission" or "well-patient" and the decision regarding which action to pursue may be motivated by increasing the probability of achieving such a diagnostic state.

The physician then assesses the result of the action to obtain a value for one or more results associated with the action, as previously described. The action performed on the patient may or may not have resulted in a desirable outcome such as the successful diagnosis of the condition and/or the successful treatment of the condition.

Next, the electronic health record of the patient is updated by the physician or a human or automated agent of the physician entering the action and the one or more results of the action. Based on the now available updated patient information, the above steps may be re-executed, until a desirable outcome is reached. Because the information available about the patient after the execution of the action has changed, the next possible actions are informed not only by the initially available basic information about the patient, but also by the newly acquired information obtained from performing the action and assessing the results.

The process described in FIG. 2 thus incorporates incrementally arriving pieces of information from the diagnostic or therapeutic process. Above described process is thus based on Bayesian interference: At each step in the care of a patient, the starting probability that a given diagnosis would be ascribed to be a condition of the patient according to the standard of care reflected in the electronic health record database (110) is a prior probability. The revised probability after obtaining a value of a result from some action is a posterior probability.

For the application of Bayesian interference to clinical medicine, the patient may have more than one concurrent condition. Each concurrent condition may affect the result(s) of a given diagnostic test, potentially confounding the interpretation of those result(s) in considering other items of the differential diagnosis in the same patient. This problem may be overcome by considering the expected effects of previously identified conditions on the results of any and all actions that may be performed in the course of evaluation and/or treatment. For example, if the patient has already been diagnosed as having one or more conditions, any complaint or test result that is inconsistent with such conditions(s) may be indicative of and should be interpreted as a possible new conditions in that patient. Ideally, the new conditions would be identified as the combination of two conditions, i.e., the previously identified one and the new, concurrent condition under consideration. In reality, the electronic health record database is unlikely to include sufficient numbers of patients with all possible combinations of all possible conditions. In this case, it may be sufficient to temporarily exclude from consideration all results that would be abnormal as a result of prior conditions. This can be done by forcing each of the relevant cells of each relevant confusion matrix (as described below) to have a value of 1, which has the effect of rendering that particular result useless for the differential diagnosis currently under consideration.

Figure 3:
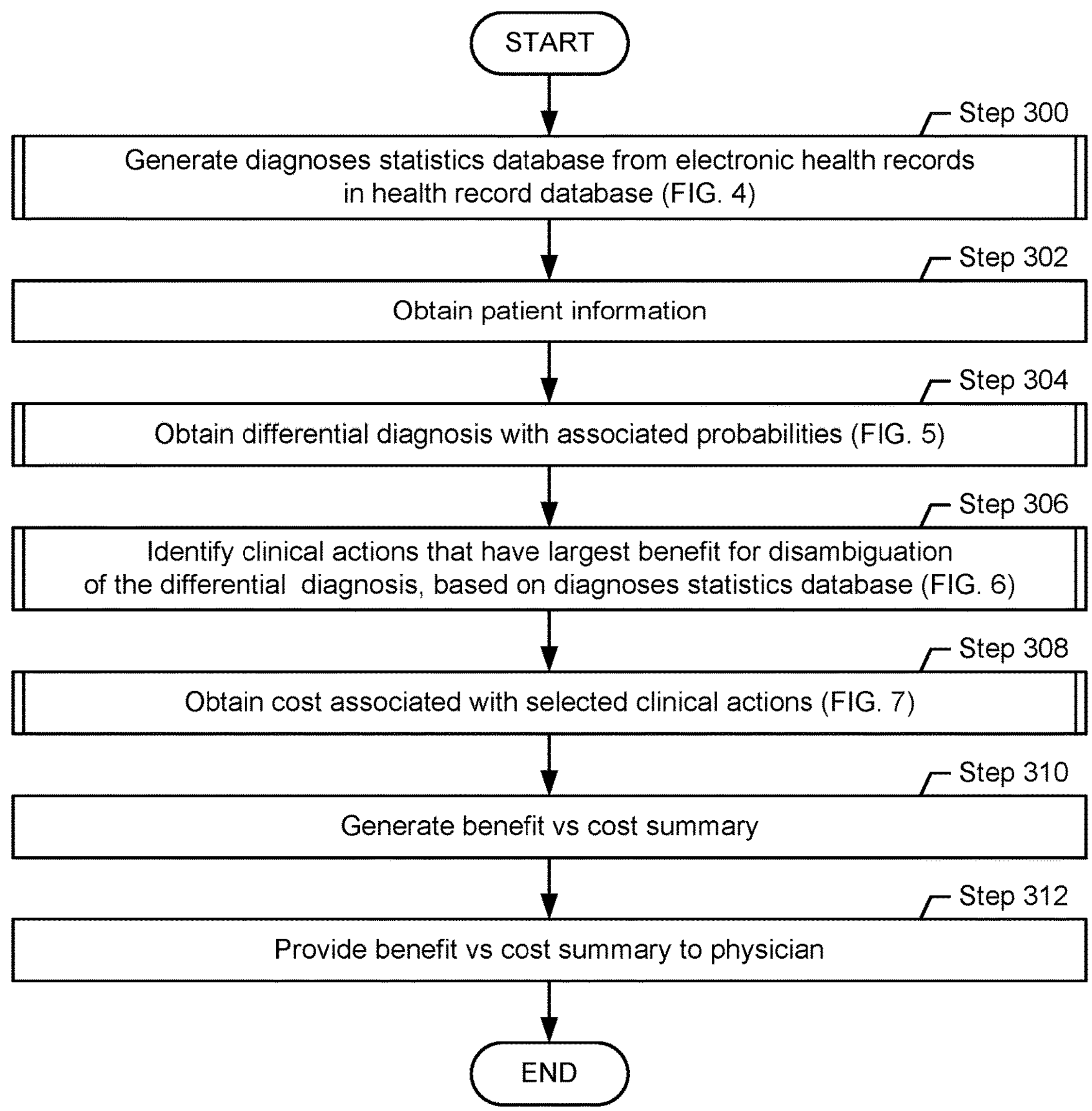
FIG. 3 shows a flowchart describing a method for processing electronic health records so as to facilitate the identification of clinical actions that may have high utility, in accordance with one or more embodiments of the invention.

Further note that the identification of a condition, as generally described in FIG. 2 and as further described in FIG. 3 may not be permanent: i) newly acquired results may make a previously designated condition untenable; ii) recognition of a new condition may call into question the accuracy of a previously designated condition, iii) treatment of a condition may render it cured and no longer pertinent. If and when these or other circumstances occur, it may be useful to iterate the process as shown in FIG. 2. This may lead to a general reassessment of the patient and may mitigate the common problem of the patient-physician relationship becoming trapped in historical and perhaps invalid assumptions.

FIGS. 3-7 show flowcharts in accordance with one or more embodiments of the invention. While the various steps in the flowcharts are presented and described sequentially, one of ordinary skill will appreciate that some or all of these steps may be executed in different orders, may be combined or omitted, and some or all of the steps may be executed in parallel. In one embodiment of the invention, the steps shown in FIGS. 3-7 may be performed in parallel with any other steps shown in FIGS. 3-7 without departing from the invention.

FIG. 3 shows a flowchart describing a method for processing electronic health records so as to facilitate the identification of clinical actions that may have high utility, in accordance with one or more embodiments of the invention.

The method of FIG. 3 may be used by a physician to provide guidance in the selection of clinical preventive, diagnostic and/or therapeutic procedures (actions) for a patient. Such guidance may be based on the cumulative experience with such procedures as captured by the electronic health record database containing the electronic health records.

As previously illustrated in FIG. 2, at least some of the steps of the method of FIG. 3 may be repeatedly executed to obtain incrementally updated guidance in the selection of actions to be performed on the patient.

Turning to FIG. 3, in Step 300, a diagnoses statistics database is generated based on information obtained from the electronic health records in the electronic health records database. The diagnoses statistics database may be generated from scratch, e.g, when the method of FIG. 3 is executed for the very first time, or alternatively, an existing diagnoses statistics database may be updated. The generation of the diagnoses statistics database, in accordance with an embodiment of the invention, is independently performed, regardless of whether other steps of the method are currently being executed to obtain guidance in the selection of actions to be performed on the patient. In other words, Step 300 may be performed asynchronously, as long as at least some form of a diagnoses statistics database exists prior to the execution of Steps 302-312. Because the execution of Step 300 can be computationally demanding, it may be performed periodically, at times when system load is low and/or the execution of Step 300 may be outsourced to a computing device different from the computing device(s) that perform Steps 302-312. A detailed description of Step 300 is provided below, with reference to FIG. 4.

In Step 302, patient information is obtained. Patient information may be obtained, for example, by a physician entering patient information into the patient's electronic health record, and/or by retrieving information that already exists in the patient's electronic health record. The obtained patient information may include any information available about the patient, including, e.g., demographic information and results obtained from performing any kinds of actions, at any time. Generally, the least information may be available when Step 302 is performed for the first time to diagnose a condition of a patient. Subsequent executions may include results from actions that have been performed on the patient, in addition to the originally available patient information. With each iteration, more information may be available.

In Step 304, a differential diagnosis with associated probabilities is obtained for the patient, based on the patient information obtained in Step 302. The differential diagnosis, in accordance with an embodiment of the invention, includes a set of some or all possible causes of the patient's chief complaint, based on the content of the health record database. In other words, any diagnosis, $D_n$, that exists in any one of the electronic health records in the health record database may be included in the differential diagnosis. Each of the diagnoses included in the differential diagnosis are accompanied by a probability, $P(D_n)$, indicating the likeliness of the diagnosis, $D_n$, being the condition of the patient. A diagnosis may be excluded from the differential diagnosis if its probability is below a consideration threshold $P_{consideration}$, thus limiting the number of diagnoses in the differential diagnosis to reasonably likely diagnoses. A detailed description of Step 304 is provided below, with reference to FIG. 5.

In Step 306, actions that have the largest benefit for disambiguation of the differential diagnosis are identified, based on information stored in the diagnoses statistics database. More specifically, for current values, $P(D_n)$, the diagnoses statistics database is queried for actions whose results are likely to affect $P(D_n)$. As previously discussed, an increase in $P(D_n)$ increases the likeliness that the diagnosis $D_n$ correctly identifies the underlying condition, whereas a decrease in $P(D_n)$ decreases the likeliness that the diagnosis $D_n$ correctly identifies the underlying condition. In other words, in one embodiment of the invention, actions are selected from those actions for which confusion matrices describe the usefulness of action results, for disambiguating the diagnoses in the differential diagnosis such that the likeliness increases that one or more diagnoses can be confirmed to correctly identify the condition(s) of the patient, whereas other diagnoses in the differential diagnosis can be discarded. A detailed description of Step 306 is provided below, with reference to FIG. 6.

In Step 308, costs, associated with actions identified in Step 306, are obtained. Costs may be defined broadly to include monetary expense, temporal delay and/or risk of adverse events, and costs may be uniquely defined for a given patient, or geographically. These costs may change over time or through the course of the diagnostic process. Costs include, but are not limited to money and time to perform the action and perhaps a delay before results can be obtained and, in some cases, non-insignificant risks of harm that the action itself might cause. Each of these costs may be considered as described in detail below, with reference to FIG. 7.

In Step 310, a summary of the actions is generated, based on the associated benefits and/or costs. The summary may include actions of a largest benefit, as determined in Step 306, or alternatively, the summary may include actions that are selected based on a highest benefit vs. cost ratio. The actions may be sorted by benefit or by benefit vs. cost. A set number of actions or any number of actions that provide at least a set minimum benefit or alternatively, have at least a minimum benefit vs cost ratio, may be included in the summary.

In Step 312, the benefit vs. cost summary is provided to the physician.

Based on the summary, the physician may then choose an action, and obtain a result of the action, as previously described in FIG. 2. Subsequently, the method of FIG. 3 may be repeated, and a new differential diagnosis and a new set of actions and costs may be obtained under consideration of the result.

More specifically, when a new result becomes available, it becomes part of the information contained in the electronic health record database and may subsequently be used to create an updated differential diagnosis, $D_n$, of the various conditions from the set of diagnoses that may be a condition of the patient and their current probabilities, $P(D_n)$ of being a condition of the patient. If $P(D_n)$ exceeds a threshold value, $P_{conclusion}$, then that diagnosis may be considered to be confirmed to be a condition of the patient. If P(Dn) falls below a threshold value $P_{consideration}$, then it may be excluded as a diagnosis actively under consideration. The physician may concur with or reject this conclusion or exclusion and may use an input tool associated with the GUI to do so.

Figure 5:
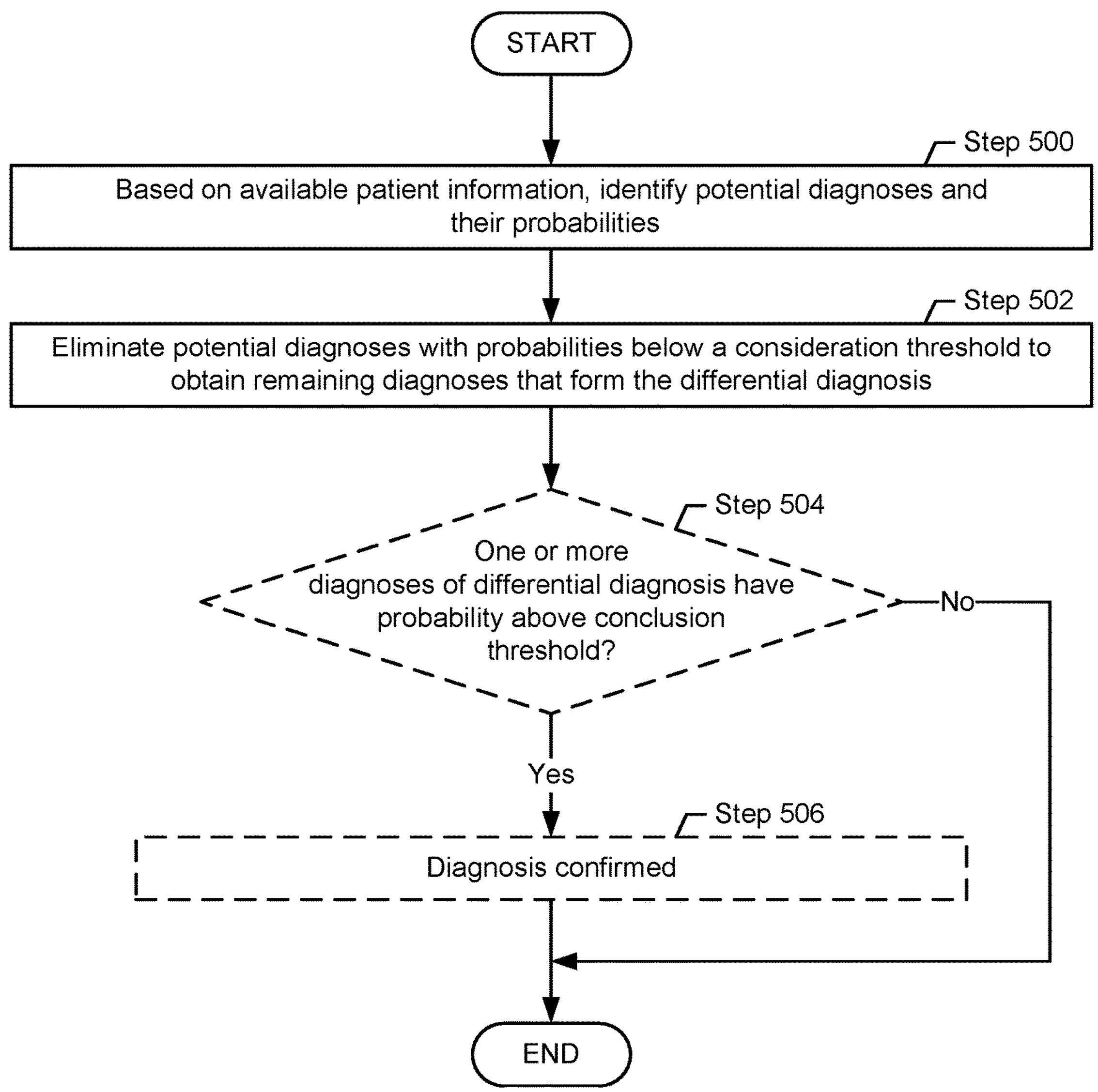
FIG. 5 shows a flowchart describing a method for obtaining a differential diagnosis for a specific patient, in accordance with one or more embodiments of the invention.

The set of $D_n$ and $P(D_n)$ may be recomputed at the beginning of each iteration, in Step 304 and as further illustrated in FIG. 5. As a result, diagnoses that were previously confirmed or excluded may need to be reconsidered if, for example, the patient has not responded as expected to a prescribed treatment. This process may continue until all intermediate values $P(D_n)$ have changed to either exceed their respective threshold value $P_{conclusion}$ or fall below the value $P_{consideration}$. Ultimately, if a diagnosis is confirmed by the physician, it may be added to the electronic health record of the patient, as a condition of the patient, thereby making that information available for future use (on the same patient or on a different patient), in accordance with an embodiment of the invention. If future treatment or evaluation determines that this diagnosis was erroneous, the electronic health records may be adjusted to reflect this.

The subsequently described FIGS. 4-7 include steps that involve the processing of data. The mathematical units used to report these data, e.g., clinical test data, are often arbitrary. They might reflect some canonical physical property in particular units of measurement, e.g. pressure as $N/m^2$ (Pascals in the metric system) or $lb/in^2$ (English system). Commonly they reflect values that depend on standardized reagents and procedures rather than canonical physical properties, for example IU (International Units of enzymatic activity in moles/s) or ACT (activated clotting time in seconds). The significance of any particular datum D tends to depend on how far it lies from the range of data that would be obtained from healthy, comparable individuals, which range may be expressed by a mean $M_H$ and a standard deviation $S_H$. The signed, relative magnitude of the deviation of D from healthy is given by $$(D-M_H)/M_H,$$

which can be expressed as a multiple of the variance $(S_H/M_H)$, resulting in a normalization function:

$$(D-M_H)/S_H.$$

The result values from healthy, comparable individuals required to compute $M_H$ and $S_H$ may be obtained by identifying from the electronic health record database (110) the electronic health records (112) of individual patients whose condition is identified as "well-patient" or a similar diagnosis indicating the absence of disease or abnormality. Values expressed in these signed, normalized units will directly reflect the number of standard deviations away from healthy in either the positive or negative direction. Accordingly, while this may not be specifically indicated, normalizations may be performed on any data that are processed when performing any of the subsequently described operations.

Figure 4:
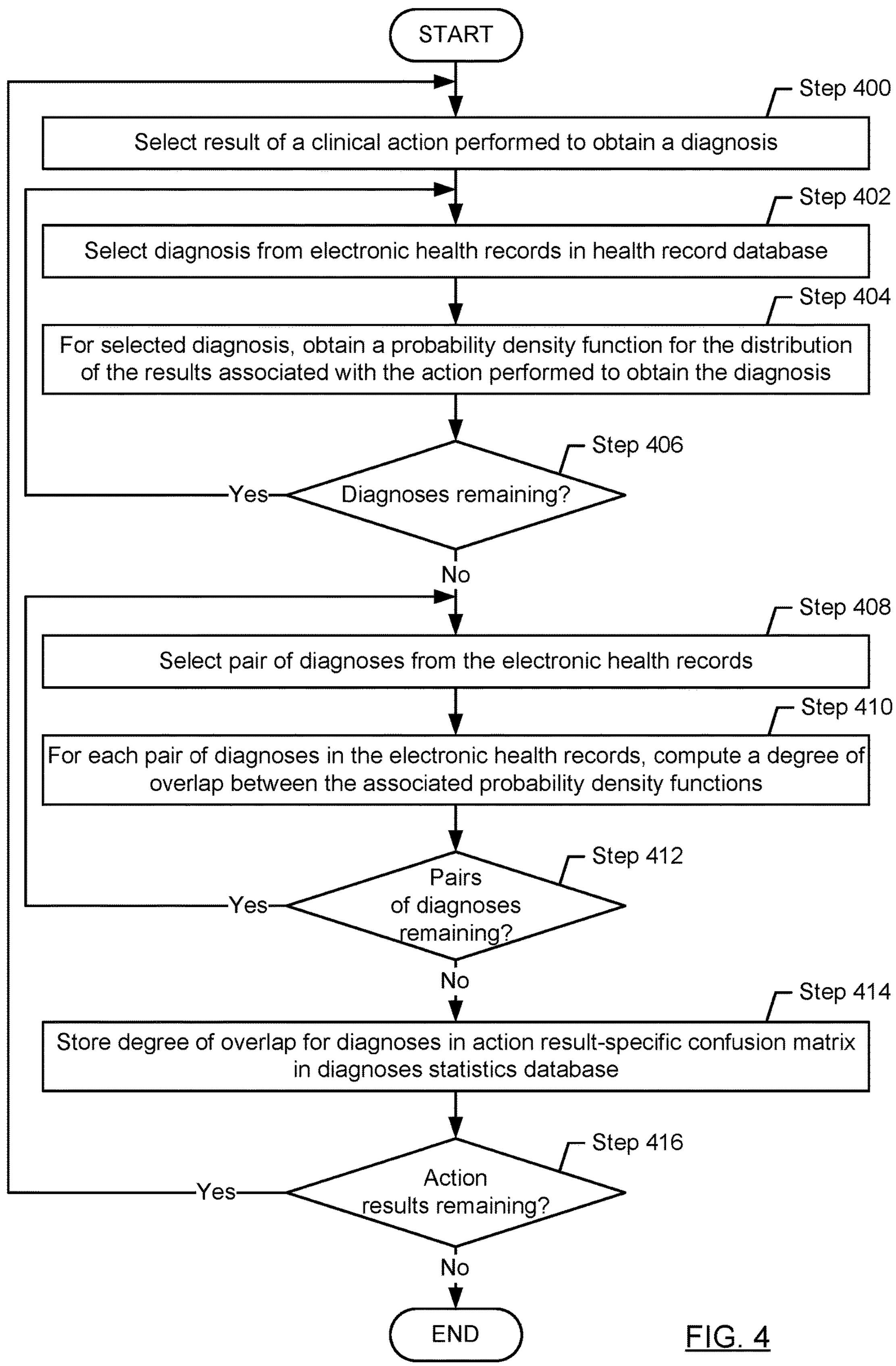
FIG. 4 shows a flowchart describing a method for generating a diagnoses statistics database from content of electronic health records, in accordance with one or more embodiments of the invention.

FIG. 4 shows a flowchart describing a method for generating a diagnoses statistics database from content of electronic health records, in accordance with one or more embodiments of the invention. Steps of the method of FIG. 4 may be executed when initially establishing the diagnoses statistics database, but also when updating the diagnoses statistics database. In one embodiment of the invention, the execution of other methods, e.g., the methods described in FIGS. 5-7, depends on the availability of the statistical information in the diagnoses statistics database. Without prior execution of the method described with reference to FIG. 4, the vast amount of information in the electronic health record database would be inaccessible, or in the best case it would be highly cumbersome and time-consuming to extract, prior to the execution of the methods described in FIGS. 5-7. Accordingly, the method of FIG. 4 enhances the information stored in the electronic heath record database in a manner making it accessible for processing according to the methods of FIGS. 5-7.

Turning to FIG. 4, in Step 400, a result of an action is selected for the execution of the subsequently performed steps, and in Step 402, a diagnosis is selected from the electronic health records. The selection of results of actions and diagnoses is not limited to particular results and actions, respectively. Any result and any diagnosis that exists in any one of the electronic health records may be selected, regardless of how frequently the result and the diagnosis, respectively, occur. For example, a selected result of an action may only exist in a single health record specific to a particular patient, or it may exist in many health records associated with many different patients. If the electronic health record database is continuously growing with the addition of new electronic health records, then diagnoses and actions that were not listed in the diagnoses statistics database (130) at one point in time may be found there at a later point in time.

In Step 404, a probability density function is obtained for the distribution of results associated with the action performed to the selected diagnosis. In other words, all values of a particular result (the result selected in Step 400) are gathered from all health records in which the result appears in conjunction with the selected diagnosis. Results that were not obtained in conjunction with the selected diagnosis (but potentially in conjunction with other diagnoses) may be ignored. The probability density function may be established from any number of results, depending on how many results are found, in conjunction with the selected diagnosis. The probability density function (PDF) may be obtained as follows. For a given mean $\overline{x}_{A_i R_j D_n}$ and standard deviation $\sigma_{A_i,R_j,D_n}$, where $A_i$ denotes the i-th action, $R_j$ denotes the j-th result, and $D_n$ denotes the n-th diagnosis, $$PDF_{A_i,R_j,D_n}(x) = \frac{1}{\sqrt{2\pi\sigma^2_{A_i,R_j,D_n}}} e^{-\frac{\left(x-x_{A_i,R_j,D_n}\right)^2}{2\sigma^2_{A_i,R_j,D_n}}}. \quad (1)$$

Statistical data on the distribution of values of a result, $R_j$, arising from an action, $A_i$, as recorded in the electronic health records for a given differential diagnosis, $D_n$, may thus be summarized in probability density functions for continuous data or in probability mass functions for discrete data, as described above. Referring to eq. (1), if these data are found to be normally distributed, then the probability density function can be computed from the mean and standard deviation of the values of the result for a given differential diagnosis. Other probability density functions for different types of distributions may be obtained for continuous variables or other probability mass functions may be obtained for discrete variables based either directly on the empirical data in the electronic health records or summary statistics of these data, without departing from the invention.

In Step 406, a determination is made about whether any diagnoses for which Step 404 has not yet been executed are remaining. If such diagnoses are remaining in the electronic health records, the method may return to Step 402 to select another diagnosis. If no such diagnoses are remaining, the method may proceed to Step 408.

Once the execution of the method reaches Step 408, probability functions have been established for all diagnoses associated with the result selected in Step 400.

In Step 408, a pair of diagnoses is selected. The pair is selected from the diagnoses obtained from the electronic health record, for which probability density functions were obtained in Step 404.

In Step 410, a degree of overlap is obtained for the probability density functions associated with the pair of diagnoses selected in Step 408. The degree of overlap may be obtained as follows.

For continuous results, $$DO_{A_i,R_j,D_{m,n}}=\int\sqrt{PDF_{A_i,R_j,D_m}(x)\cdot PDF_{A_i,R_j,D_n}(x)}dx, \tag{2}$$

where DO denotes the degree of overlap obtained for the pair of selected diagnoses $D_m$ and $D_n$.

For discrete results, $$DO_{A_i,R_j,D_{m,n}}=\Sigma_x\int\sqrt{PMF_{A_i,R_j,D_m}(x)\cdot PMF_{A_i,R_j,D_n}(x)}. \tag{3}$$

In Step 412, a determination is made about whether additional pairs of diagnoses are remaining. If additional pairs of diagnoses are remaining, the method may return to Step 408 to repeat Steps 408 and 410 for the remaining pair(s) of diagnoses. If no additional pairs of diagnoses are remaining, the method may proceed to Step 414.

Once the execution of the method reaches Step 412, degrees of overlap have been obtained for any combination of any diagnosis with any other diagnosis, for a specific result.

In Step 414, the degree of overlap for all pairs of diagnoses, for the selected action result, is stored in a confusion matrix in the diagnoses statistics database. If the probability density functions of a pair of diagnoses have little overlap, the confusion matrix value in the intersection cell of the matrix is low; if the probability density functions overlap completely, the confusion matrix value of that cell is 1.

In Step 416, a determination is made about whether any actions for which Steps 400-414 have not yet been executed are remaining. If such actions are remaining in the electronic health records, the method may return to Step 400 to select another action. If no such action is remaining, the execution of the method may terminate.

After the completion of the method of FIG. 4, confusion matrices may exist for any result obtained from performing actions. Each of these confusion matrices is result-specific and encodes the degree of overlap between the probability density functions for all diagnoses for which Steps 400-416 were performed.

While in the method described in FIG. 4, all results values of all actions are used for the generation of probability density functions, alternatively, certain limitations may be imposed. For example, certain electronic health records may be excluded, e.g., for selected patient groups, based on demographic factors such as sex, age, ethnicity, etc. without departing from the invention. Embodiments of the invention thus also allow to selectively perform the described methods for specific groups of patients, which may be useful, for example, if lab results are analyzed, which are known to depend on demographic factors.

FIG. 5 shows a flowchart describing a method for obtaining a differential diagnosis for a specific patient, in accordance with one or more embodiments of the invention. As previously described, the method may be repeatedly executed, in particular, whenever new data about the patient becomes available, e.g., after obtaining a new result from performing an action on the patient.

In Step 500, potential diagnoses of the patient's condition are identified based on the currently available patient information. The available patient information may vary. When the method of FIG. 5 is initially performed, only basic information about the patient may be available. For example, the patient demographics, patient complaints and vital signs may be available. Bayesian inference can then be applied to the electronic health records database or to the probability density functions in the diagnoses statistics database in order to identify the most likely diagnoses and their associated probabilities. In subsequent executions of the method of FIG. 5, the additional information that becomes available, e.g., after obtaining a new result from performing an action on the patient, may be considered as well to obtain the potential diagnoses according to Bayesian inference. That is to say that the prior probabilities of all diagnoses are adjusted according to the probability in the electronic health record database (110) that a patient with each of those condition would exhibit the value of the new result just obtained, thus becoming posterior probabilities, as further described below with reference to FIG. 6.

Any diagnosis, $D_n$, that exists in any one of the electronic health records in the health record database may be included in the differential diagnosis. Each of the diagnoses included in the differential diagnosis is accompanied by a probability, $P(D_n)$, indicating the likeliness of the diagnosis, $D_n$, being the condition of the patient. Many potential diagnoses may be identified in Step 500. These diagnoses may have any probability, that may range from highly likely to highly unlikely.

In Step 502, potential diagnoses with low probabilities are identified and eliminated. A diagnosis may be excluded from the differential diagnosis if its probability is below a consideration threshold $P_{consideration}$, thus limiting the diagnoses in the differential diagnosis to reasonably likely diagnoses.

In Step 504, a determination is made about whether one or more of the diagnoses in the differential diagnosis reach a conclusion threshold, $P_{conclusion}$. The threshold value of $P_{conclusion}$ may be set at any level deemed to be indicative of certainty that the associated diagnosis matches the underlying condition. The threshold value of $P_{conclusion}$ may further be different for individual diagnoses to take into consideration unique risks of false positives of each candidate diagnosis. The threshold value of $P_{consideration}$ may also be adjusted depending on the iterative stage of the execution of the entire method of FIG. 3 and/or the number of items currently in the differential diagnosis of the patient.

In Step 506, if the conclusion threshold is reached by a particular diagnosis, the diagnosis is assumed to be confirmed.

Steps 504 and 506 are optional. Specifically, the execution of Steps 504 and 506 may be omitted in embodiments of the invention that are designed to be purely advisory. In such cases, it is the physician who decides whether a diagnosis is confirmed or not.

Figure 6:
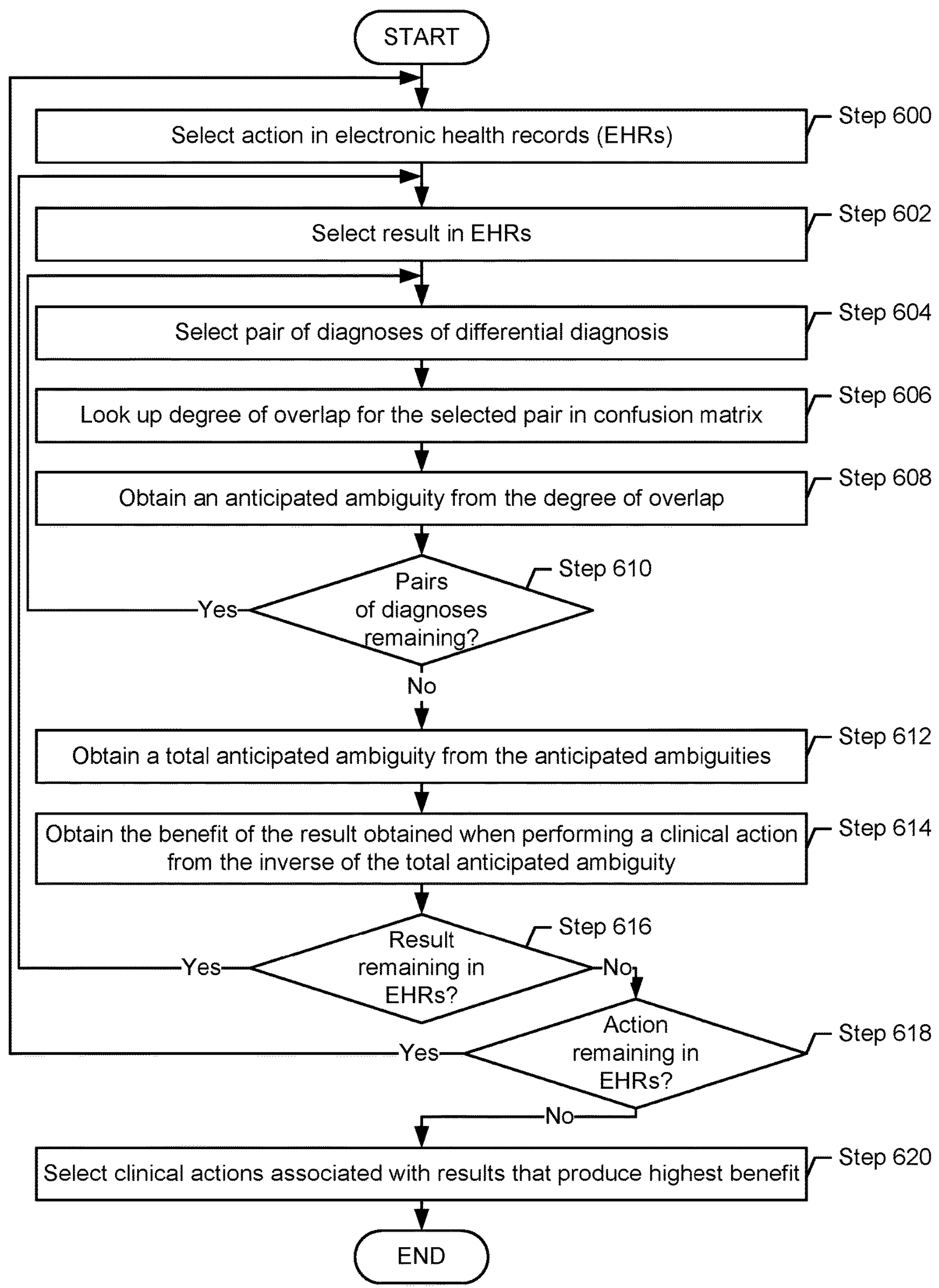
FIG. 6 shows a flowchart describing a method for computing the relative diagnostic, therapeutic or preventive benefits of pursuing various clinical actions with a specific patient, in accordance with one or more embodiments of the invention.

FIG. 6 shows a flowchart describing a method for computing the relative diagnostic, therapeutic or preventive benefits of pursuing various clinical actions with a specific patient, in accordance with one or more embodiments of the invention. In other words, in FIG. 6, the optimal action to identify the condition of a patient is determined by finding the result that will most likely disambiguate the current differential diagnosis. This may be performed using the confusion matrices, in which, for each result of an action, the rows and columns represent all of the diagnoses, as previously described with reference to FIG. 4.

Each element of the differential diagnosis, $D_n$, may be associated with a prior probability $P(D_n)$ that it is a condition of the patient, based initially on minimal information such as the patient's complaint and demographic information such as age and sex, as described in FIG. 5. Actions may be used to further disambiguate the differential diagnosis, if these actions are properly chosen. In other words, based on an action, posterior probabilities may be obtained that are more likely to indicate that a particular diagnosis is or is not the condition of the patient. The method of FIG. 5 may be used to identify such actions.

Turning to FIG. 6, in Step 600, an action is selected in the electronic health record, and in Step 602, a result of the action is selected. The action and the result may be selected from those actions and results, respectively, for which confusion matrices were previously generated.

In Step 604, a pair of diagnoses is selected from the differential diagnosis, and in Step 606, the degree of overlap is looked up in the confusion matrix associated with the result, for the pair of selected diagnoses.

In Step 608, an anticipated ambiguity is obtained from the degree of overlap. The anticipated ambiguity may be obtained as follows.

Given the prior probabilities $P(D_m)$, $P(D_n)$ of diagnoses $D_m$ and $D_n$, respectively, $$AA_{A_iR_jD_{m,n}}=DO_{A_i,R_j,C_{m,n}}P(D_m)P(D_n), \quad (4)$$

with AA denoting the anticipated ambiguity, $A_i$ denoting the i-th action, $R_j$ denoting the j-th result, and $D_{m,n}$ denoting the pair of the m-th and n-th diagnoses. In other words, the anticipated ambiguity, AA, of obtaining a given result at that time may be computed by weighting the degree of overlap DO in each cell of the confusion matrix by the product of the two prior probabilities of the diagnoses representing the row and column addresses of the cell, as shown in eq. 4.

In Step 610, a determination is made about whether pairs of diagnoses are remaining. If additional pairs of diagnoses are remaining, the method may return to Step 604 to repeat Steps 606 and 608 for the remaining pair(s) of diagnoses. If no additional pairs of diagnoses are remaining, the method may proceed to Step 612.

Once the execution of the method reaches Step 612, anticipated ambiguities have been obtained for any possible pairs of diagnoses in the differential diagnosis, for a specific result of a specific action.

In Step 612, a total anticipated ambiguity is obtained from the anticipated ambiguities. The total anticipated ambiguity may be obtained as follows.

$$TAA_{A_iR_j}=\Sigma_m\Sigma_n AA_{A_i,R_j,D_{m,n}}, \quad (5)$$

with TAA denoting the total anticipated ambiguity obtained for all pairs of diagnoses in the differential diagnosis.

In Step 614, the benefit of the result obtained when performing an action is determined. In one embodiment of the invention, the benefit is the inverse of the total anticipated ambiguity.

In Step 616, a determination is made about whether any results for which Steps 604-614 have not yet been executed are remaining. If such results are remaining in the electronic health records, the method may return to Step 602 to select another result. If no such result is remaining, the method may proceed to Step 618.

In Step 618, a determination is made about whether any actions for which Steps 602-616 have not yet been executed are remaining. If such actions are remaining in the electronic health records, the method may return to Step 600 to select another action. If no such action is remaining, the method may proceed to Step 620.

Once the execution of the method reaches Step 620, benefits have been obtained for any possible pairs of diagnoses in the differential diagnosis, for any existing result of any action.

In Step 620, actions associated with results that produce the highest benefit, for disambiguating the differential diagnosis, may be selected, based on the associated probabilities. The selected actions, along with the associated probabilities may be compiled in a list in which the actions may be ordered based on the associated probabilities. The selection may be performed in order to limit the number of actions to be subsequently evaluated for cost, as described with reference to FIG. 7, and/or to limit the number of actions to be presented to the physician. Actions with a benefit above a certain threshold may be selected and/or the selected actions may be limited to a maximum number of selected actions.

The result with the highest benefit is the most useful one to obtain by performing the action that gives rise to the result, in accordance with an embodiment of the invention. It may be advantageous to perform the weighting and summation steps in eq. (4) and (5) on only those diagnoses that are currently part of the differential diagnosis for the patient at hand. That is to say that the benefit of an action is the degree to which the results of that action are likely to shift the probabilities $P(D_n)$ of the various diagnoses $(D_n)$ in the differential diagnosis under consideration.

Figure 7:
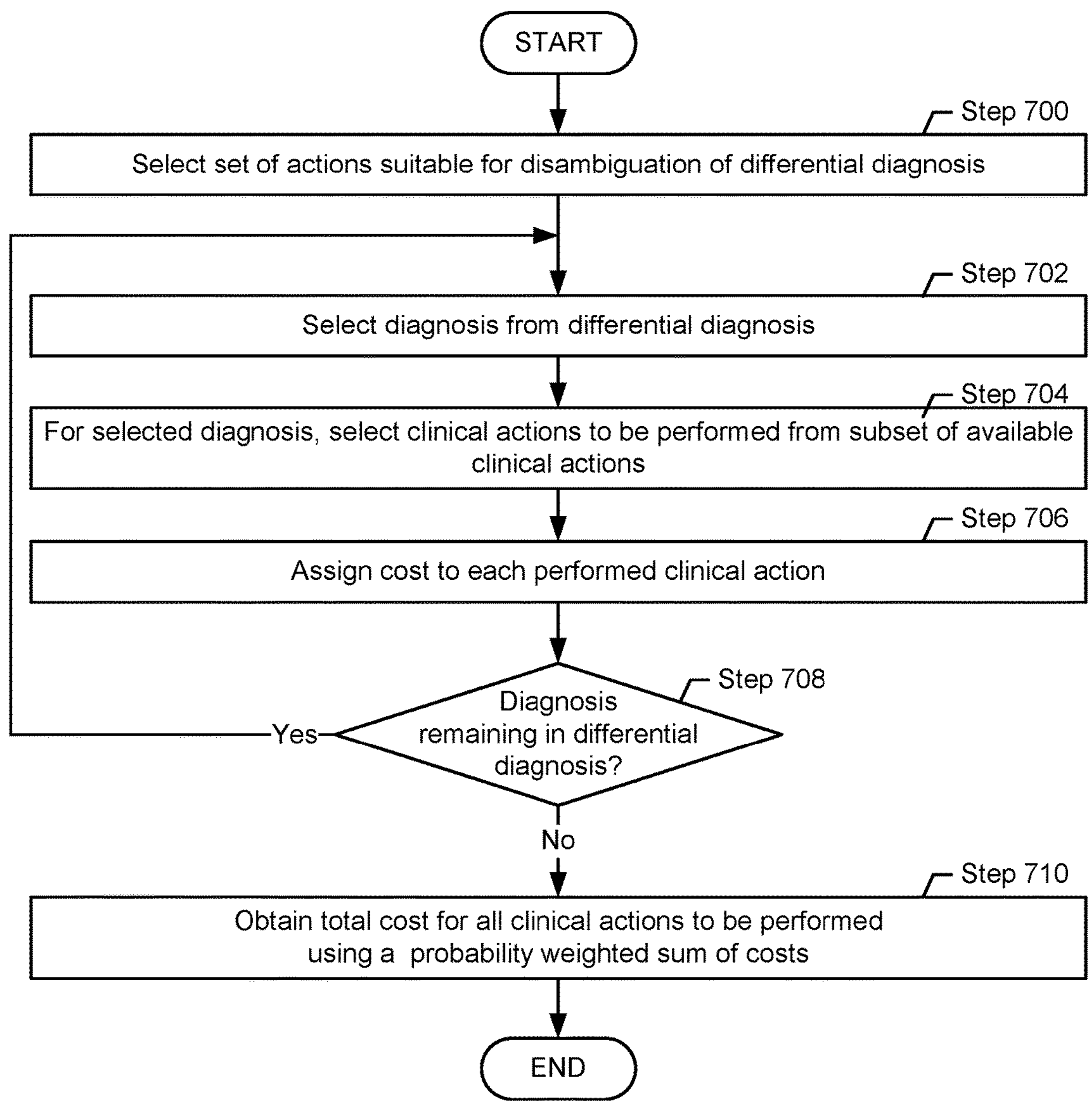
FIG. 7 shows a flowchart describing a method for computing costs associated with performing clinical actions, in accordance with one or more embodiments of the invention.

FIG. 7 shows a flowchart describing a method for computing costs associated with performing clinical actions, in accordance with one or more embodiments of the invention.

Any action that might be taken with a patient has a cost, whose value may depend on various factors as detailed below. The physician's decision to pursue one of the possible actions that he/she might undertake may be informed by maximizing the ratio of benefit to cost, thereby maximizing the efficiency of health care delivery. Because any given action may be associated with multiple results, the benefit of an action represents the sum of the benefits of its various results. The efficiency of an action is this sum of benefits divided by the cost of the action. The physician may use the relative efficiencies to decide which action to take. This decision may also involve subjective considerations not captured by the database or outcome measures, hence the advisory nature of described methods.

The cost function for a given action may include relatively simple and constant terms such as financial expense to perform the action (e.g. collect a blood sample and perform a battery of chemical tests on it) as well as complex terms such as risks and delays, whose contribution depends on the as-yet-unknown condition of the patient. All of the terms in the function must be converted to common units, which we assume to be dollars in the examples below, but which could be any units, including normalization to be dimensionless.

Risks and delays may be converted into dollar-denominated costs by monetizing their consequences to the patient. This requires converting time and morbidity into money. Such a conversion is well-known to the healthcare insurance industry, which uses Quality Adjusted Life Years (QALYs) to evaluate the relative outcomes of various treatments that have different monetary costs. The beneficial effects of a treatment of a condition might be to improve the quality of a patient's remaining natural life or to delay death from a fatal disease or both. Any delay in diagnosing the condition and instituting treatment would delay those benefits. The risks of a diagnostic procedure or treatment include adverse events that might reduce the quality and/or duration of the patient's remaining life and that might incur consequential costs associated with diagnosis and treatment of such adverse events. Converting QALYs to dollars requires a conversion factor, which tends to vary from one society and health care system to another. For example, a society might deem actions that cost less than $10,000 to be justifiable if they produce one QALY of benefit, such as by extending healthy life for one year or by making a 10% improvement in quality of life for ten years. This implicitly values 1 QALY=$10,000.

When benefits accrue at different times, it is common practice in economics to apply a discount factor, such that future benefits are valued less highly than immediate benefits. In one embodiment of the invention, a discount factor may be introduced into the computation of costs and benefits. That value of that discount factor may be systematically varied in order to evaluate different types of healthcare. For example, a large discount factor will cause the computations described below to weight more heavily the immediate consequences of a given action, which may tend to prioritize actions that would solve the patient's current complaint. Conversely, a small discount factor will cause the computations described below to weight more heavily those actions that might reduce costs or provide benefits over the lifetime of the patient, which may be more appropriate as part of a general consultation with a well-patient.

Turning to FIG. 7, in Step 700, a set of actions, suitable for the disambiguation of the differential diagnosis is selected. The selection may include the actions identified as described in FIG. 6, or a subset of these actions.

In Step 702, a diagnosis is selected from the differential diagnosis.

In Step 704, a subset of actions, suitable for confirming the selected diagnosis, is selected. Such actions may include actions that are particularly helpful in disambiguating the differential diagnosis, selected from the actions obtained after the execution of the method of FIG. 6.

In Step 706, a cost is assigned to each of those actions, based on the various costs associated with the action as previously discussed.

In Step 708, a determination is made about whether one or more diagnoses for which Steps 704 and 706 have not yet been executed are remaining in the differential diagnosis. If such diagnoses are remaining, the method may return to Step 702 to select another diagnosis. If no diagnosis is remaining, the method may proceed to Step 710.

In Step 710, the total cost for all actions to be performed is obtained, using a probability weighted sum of all costs.

The method of FIG. 7 may be performed, for example, using a Markov chain-like approach, as subsequently illustrated in detail with reference to FIG. 8.

Figure 8:
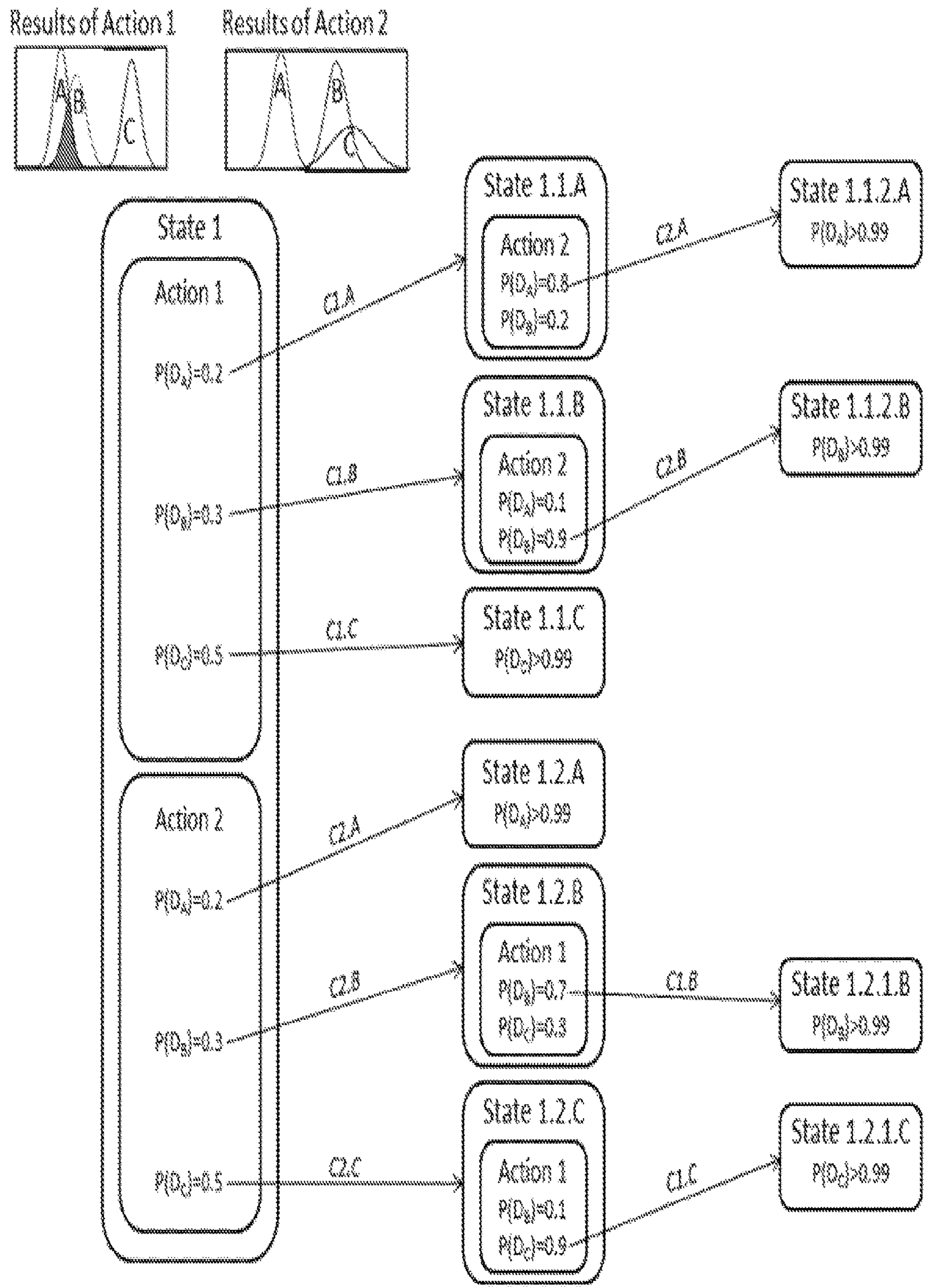
FIG. 8 shows an exemplary calculation for obtaining costs associated with a set of possible states and actions that may lead to determining that a specific patient has a specific condition, in accordance with one or more embodiments of the invention.

FIG. 8 shows an exemplary calculation for obtaining costs associated with a set of possible states and actions that may lead to determining that a specific patient has a specific condition, in accordance with one or more embodiments of the invention.

It may be advantageous first to select those actions that have already been determined to have high benefits, in order to limit the amount of computing power required to estimate the effective cost of each such action. The consequences of a given risk or delay may depend on the actual condition(s) of the patient, including the as-yet-unknown condition that is the subject of the differential diagnosis. For example, it may be much more important immediately to treat one condition than another, so delays from testing have different costs for patients with each of those conditions. The effective cost may be evaluated using a branching, non-recursive Markov chain model, which prorates and then integrates all the costs of the current and future steps according to their probabilities of being incurred.

In the example illustrated in FIG. 8, the three alternative diagnoses $D_A$, $D_B$ and $D_C$ have different prior probabilities based on prior data to which we have given illustrative values: $P(D_A)=0.2$, $P(D_B)=0.3$ and $P(D_C)=0.5$, respectively. Suppose that diagnostic action 1 and action 2 both have substantial benefit as defined above, i.e., they both lead to a definitive diagnosis in which the probability exceeds 99% for at least one diagnosis (i.e. $P_{conclusion}=0.99$). The graphs show the probability density functions for obtaining a given value of the result of an action (abscissa) for patients in the electronic health record database who actually had conditions A, B or C. It can be seen that action 1 is likely to distinguish condition C from A and B but not A and B from each other (large overlap), while action 2 is likely to distinguish condition A from B and C but not B and C from each other. The goal is to optimize efficiency, so the benefit of the action must be divided by the cost of the action, but the cost depends on what condition the patient actually has, which is not yet known. The cost of each action for a patient with each condition is prorated by the prior probability at that state that the patient has that condition. If we assume that a patient with a given condition will obtain the most likely value of test result for such patients (the mean value in the normal distributions of results illustrated), it is possible to compute the probability that a new result will lead to a definitive diagnosis of that condition or will require further diagnostic action to confirm or refute that diagnosis.

Referring to the state diagram in FIG. 8, if diagnosis C (currently the most likely) is the true condition of the patient and action 1 were taken, then it would entail cost C1.C and would lead to a confirmation of diagnosis C with probability $P(D_C)>0.99$. If diagnosis A is the true condition of the patient and action 1 were taken, then it would entail cost C1.A. The most likely result would lead to State 1.1.A, in which diagnosis C has been excluded and the probability of diagnosis A is now 0.8, and the probability of diagnosis B is 0.2. If diagnosis B is the true condition of the patient and action 1 were taken, then it would entail cost C1.B. The most likely result would lead to state 1.1.B, in which diagnosis C has been excluded and the probability of diagnosis A is now 0.1 and the probability of diagnosis B is 0.9. For both state 1.1.A and state 1.1.B, action 2 is useful because its results are likely to distinguish between the only two diagnoses currently being entertained. A patient who actually has condition A will now experience cost C2.A and likely will arrive in state 1.1.2.A in which diagnosis A is confirmed. A patient who actually has condition B will now experience Cost 2.B and likely will arrive in state 1.1.2.B in which diagnosis B is confirmed.

Continuing with the discussion of the state diagram shown in FIG. 8, the patient in state 1 with the prior probabilities $P(D_A)=0.2$, $P(D_B)=0.3$ and $P(D_C)=0.5$ might first be subjected to action 2 instead of action 1. If diagnosis A were actually the true condition for the patient, the cost would be C2.A and the most likely result of action 2 would be to confirm this diagnosis in state 1.2.A where $P(D_C)>0.99$. If either diagnosis B or C were the correct condition of this patient, it would be useful subsequently to perform action 1, which will most likely lead to the definitive diagnosis of the correct condition. The costs of action 1 are different for patients with different conditions and the probability of incurring them depends on the probability that the patient actually has each condition.

The most likely costs of taking either of the two available actions starting at initial State 1 may now be compared. The probability weighted total cost of starting with action 1 is 0.2*(C1.A+C2.A)+0.3*(C1.B+C2.B)+0.5*C1.C. The probability weighted total cost of starting with action 2 is 0.2*C2.A+0.3(C2.B+C1.B)+0.5(C2.C+C1.C). The benefits of starting with each action when in state 1 as computed by the method described in FIG. 6 can now be combined with the most likely costs of starting with each action as just computed by the exemplary implementation of a cost algorithm to arrive at a benefit/cost ranking that determines the order of the available actions as presented to physician. The Markov chain representing the actual states of actual patients with actual conditions and a richer set of available actions and results will usually be substantially more complex than this highly idealized example. Those skilled in the art will appreciate that the method of FIG. 7 is not limited to the example of FIG. 8.

The physician may use any or all of the types of information illustrated in FIG. 8 to decide which action to pursue. The physician might simply embark on the path with the highest benefit/cost as predicted by this statistical analysis. Alternatively, he/she might choose another path based on individual risk factors, personal professional experience or diagnostic hunches, in which case it may be advantageous to visualize all of the Markov chains and their anticipated benefits and costs at each anticipated state in order to make sure that possible diagnoses or costs have not been overlooked. After any specific action with the patient, the probabilities may be updated based on actual results according to Bayesian inference, and the physician may use this information to make further decisions about the patient's diagnosis or treatment based on a similar computation of the new Markov chain, which may include revised probabilities and the inclusion or exclusion of various diagnoses based on the revised probabilities that are now greater or lesser than $P_{consideration}$, respectively.

The use case scenarios described below are intended to provide examples of the method for identifying diagnostic and therapeutic options for medical conditions using electronic health records. These use case scenarios are for illustrative purposes only, and the method described by FIGS. 3-7 are not limited by these use cases.

Turning to the use cases, assume that the electronic health record database contains only three diagnoses related to the presenting complaint of headache: tension headache, viral encephalitis, and meningioma (non-malignant brain tumor). There are only two relevant diagnostic actions: spinal tap and MRI (magnetic resonance imaging). There are only three relevant therapeutic actions: aspirin, acyclovir (intravenous antiviral drug), and craniotomy (brain surgery to remove a tumor). In FIGS. 9A-9D, referenced by these use cases, underlined text denotes data entered into the system by the user or an agent of the user, and italicized text denotes information provided to the user by the system.

Use Case 1—Physician treating Patient (1)

Referring to FIG. 9A, after the physician enters the demographic information and presenting complaint for a new patient, the system automatically provides a list of coded diagnoses prioritized according to their probability of being a condition of the patient, plus a list of coded diagnostic actions prioritized according to their benefit/cost as determined by above-described methods. The physician may select any or all three diagnoses as plausible for this specific patient and then select the MRI test as the diagnostic action that in the physician's opinion is most reasonable for this patient.

Use Case 1—Physician Treating Patient (2)

Referring to FIG. 9B, the patient has returned after the results of the MRI test have been added to the patient's electronic health record. These results now place the probability of having a meningioma as 99%, which exceeds $P_{conclusion}$. Because the physician has accepted this as a condition of the patient, the system now displays a coded list of therapeutic actions prioritized according to their benefit/cost as determined by above-described methods. The physician may select any or all therapeutic actions that in the physician's opinion is (are) most reasonable for this patient.

Use Case 2 Patient Treating Self (Acting as Own Physician)

Referring to FIG. 9C, an individual consumer may use the system to understand, diagnose and/or treat their own health problem. After entering the demographic information and information about their problem, the system generates a prioritized list of coded diagnoses and a prioritized list of diagnostic actions that might be useful, based on the electronic health record database representing the diagnoses, diagnostic actions and results obtained with a large population of similar individuals with a similar problem. In this case, only one of the diagnostic actions, MRI, is available without a professional physician, and the system has displayed a link to a commercial provider of MRI testing that has an imaging machine in the same zipcode as the consumer. Once the results of that test are entered into the electronic health record for this consumer patient, either automatically or manually by the MRI service or the consumer patient, the system will reprioritize the list of currently likely diagnoses and provide a prioritized list of available therapeutic actions similar to those described in FIG. 9C. The consumer patient may decide to treat himself for some therapeutic actions such as taking aspirin or may seek professional care for others such as having a craniotomy.

Use Case 3—Epidemiologist Monitoring Community Health

Referring to FIG. 9D, a user of the system may be an epidemiologist charged with identifying potential threats to public health. The user interface may allow the epidemiologist to look for suspicious patterns in the electronic health records. The epidemiologist may select what type of data to examine according to their codes (e.g. D=diagnoses, T=diagnostic action, R=therapeutic action), the geographical region of interest according to zipcodes, the timeframe over which to search, and the size of the anomaly measured according to the number of standard deviations away from the expected occurrence of the code in the search population. FIG. 9D shows an example of the results of such an epidemiological search in which the diagnosis D003 for meningioma has occurred in zipcode 11111 with an incidence that is 3.0 standard deviations away from normal incidence in the overall electronic health records. Such an unusual occurrence may motivate the epidemiologist to look for environmental contaminants that may be associated with meningioma or for insurance fraud in which physicians may be billing for unnecessary medical procedures for nonexistent conditions.

Generally, one underlying assumption about the health record database is that patients, conditions, accuracy of diagnostic tests and efficacy of treatment are all distributed uniformly among the population of individuals represented in the database. Any deviation from such a uniform distribution may thus be detected. The following are examples of situations in which the uniform distribution may not be true and in which discovery of such anomalies in a subset of the database may provide valuable information for public health authorities, government regulators, law enforcement officials, insurers, politicians, etc.:

A local environmental hazard such as water pollution or a disease vector such as mosquitos could give rise to an anomalously high incidence of one or more specific diagnoses in patients living in that locale.

A laboratory may be producing inaccurate diagnostic test results for reasons of incompetence or fraud, which could give rise to an anomalously high incidence of one or more specific diagnoses in patients whose test results come from that laboratory.

A physician may be claiming but not administering treatment or may be providing inadequate treatment such as through poor physical technique or adulteration of a drug, which could result in patients under that physician's care experiencing generally poorer outcomes or incurring higher costs than patients with similar diagnoses in the database as a whole.

A group of patients may be malingering to obtain time off from work or disability insurance benefits, which could result in statistically improbable increases in the incidence of a specific diagnosis in a particular time frame or locale.

The electronic health record database will typically include metadata about the geographical location of each patient, the identity of the physician or clinic that is making diagnoses or prescribing treatment, the source of diagnostic test data, etc., all of which may be used to discover anomalies such as the above in a subset of patients who share such distinguishing characteristics. At each stage of the treatment of each patient, the above described methods compute the probability of proceeding to each of the differential diagnoses, whose probabilities each exceed $P_{consideration}$. Given a large enough subset of similar patients, simple tests well-known to anyone normally skilled in the art of statistics can be applied to determine the probability that the distribution of diagnoses in the subset of patients is consistent with that expected from the variability within the population comprising the database as a whole. If the probability is lower than some administrative criterion, that information may be used to trigger an investigation to identify the root cause, if any, of the anomaly.

Use Case 4—AutoComplete Feature in Electronic Health Record User Interface

Embodiments of the invention may be used to facilitate and improve the entry of data into the patient's electronic health record. Specifically, in the user interface, the predictive capabilities of above described methods may be employed to make terminology suggestions as the physician enters data.

One of the main problems with the currently available electronic health records is that much of the important information regarding the physician's assessment of and plans for the patient is captured in free text that is typed into or cut and pasted into the electronic health record from the physician's notes rather than captured according to standard keywords and numerical codes. Translating such free text into standard keywords and numerical codes is cumbersome and prone to errors whether done by humans or machines. Conventional graphical user interfaces with menus and tabs whereby the physician might locate standard keywords and numerical codes are available, but these are cumbersome to use, particularly when the physician is supposed to be engaged with the patient in a physical examination. The extremely wide range of medical terminology for clinical observations, diagnoses, treatments and outcomes makes it difficult to employ the sort of anticipatory word-completion software that is commonly used to facilitate selection and entry of common words in messaging applications on smart phones.

Embodiments of the invention enable an intelligent anticipatory function similar to word-completion software but much more attuned to the actual thought processes of the medical interaction as it actually unfolds with an individual patient. The probability-ordered suggestions for differential diagnosis, further testing and treatment options that may be provided by our invention may be linked to the data entry system for the electronic health care record. The physician or other health care provider may then simply select and/or concur with specific items from a list of highly relevant options instead of digging through a large hierarchy of universal medical terminology.

The use of this embodiment encourages and facilitates the utilization of standardized terminology, which will, over time, improve the quality of the electronic health records. Such an improvement will, in turn, result in an increased usefulness of the electronic medical records for diagnostic and therapeutic purposes, as previously described, thus facilitating widespread and efficient utilization of the previously described methods.

Use Case 5—Health Maintenance

Embodiments of the invention may be used in a health maintenance environment in which the patient is actually a client whose health is being regularly monitored, as opposed to a patient presenting with a specific complaint. In such a care relationship, the client will still have various probabilities of having various medical conditions that are occult or otherwise not among the patient's complaints and that might be detected by the appropriate screening test. The goal of the health maintenance relationship is to maximize the well-being of the client over the client's entire lifetime, which may be quantified as maximizing the probability of the diagnosis "well-patient". The cost/effectiveness of performing a given action should be evaluated against the cost/effectiveness of the action of simply scheduling a next regular check-up, at which time symptoms might be more apparent or a test might be more likely to provide definitive results. Thus the electronic health record database may be used to decide on a patient-by-patient basis how to practice preventive medicine. For example, a patient in a demographic group with a certain probability of having breast cancer might be advised to have or to forego a mammogram based on the distribution of results of such a diagnostic procedure in other, similar patients, some of whom will have been saved by an early diagnosis of cancer and others of whom will have been subjected to unnecessary surgery with consequent adverse events. The patient might be advised not to have the mammogram but instead to change her diet and/or to avoid hormone replacement therapy and/or to perform regular self-examination and/or to return for another check-up after a specific interval. Some of these possible actions might themselves have adverse consequences for the general health of the patient. For example, foregoing hormone replacement therapy might increase the probability of osteoporosis with increased risk of bone fractures. Weighing the relative risks and costs of breast cancer and broken hips may be better informed by obtaining additional information about this patient, such as a bone mineral density scan. A low value of bone mineral density in this specific patient might be addressed by proceeding with hormone replacement therapy or by starting an exercise program or by increasing dietary calcium or a combination of these and other measures. Our invention may be used to suggest any or all of these possible courses of action and to provide information to the physician about the relative cost-effectiveness of each at any time.

More generally, the treatment in a health maintenance environment is likely to include advice about lifestyle choices that might maximize the well-being of the client over the client's entire lifetime. As described in more detail below, the utility of such measures may be quantified according to the probabilities of being in various healthy or diseased states and the costs of morbidity and mortality of being in various diseased states, which costs the algorithm may seek to minimize over the projected life of the patient. These options and suggestions may be prioritized and their utility quantified according to data drawn from the database of all electronic health records, thereby motivating the physician to provide them and the patient to consider them more seriously than general personal advice.

Use Case 6—Accomplishing Societal Goals

Embodiments of the invention may be used to accomplish societal goals, for example based on epidemiological considerations. There are certain medical conditions for which the cost of treating or not treating an individual patient is low but which entail large societal costs. One example is the use of antibiotics to treat a complaint that has a high probability of arising from a nonbacterial and self-limiting viral infection. In such a case, the cost of the antibiotic and the risk to the patient are both very low, but widespread and long-term overuse of antibiotics tends to give rise to antibiotic-resistant pathogens that may cause severe and untreatable diseases in other individuals. In a second example, consider that a complaint may arise from a highly contagious disease such as measles that cannot be treated effectively in the patient but can be prevented from spreading by quarantine. Because there is no treatment, there is no benefit to making the specific diagnosis for the individual patient. Even with the correct diagnosis in hand, imposing a quarantine provides no benefit to the immediate patient. The above scenarios and others like them are related to what economists call "the tragedy of the commons," in which actions or inactions that are desirable or beneficial for a single individual are counterproductive when performed by large numbers of individuals and that generate costs that are born by other individuals. One effective means of discouraging such counter-productive actions is to tax them so as to raise their costs to reflect those future costs to society. The present invention may incorporate such measures by adding a tax in the form of a virtual cost to the real cost of performing or not performing an action. For the first example above, the total cost of prescribing the potentially unnecessary antibiotic may be increased by a virtual tax whose value is decided upon by external agents such as lawmakers, healthcare regulators or medical societies. For the second example above, the cost in QALYs for an undiagnosed but highly contagious disease could be magnified to take into account the consequences of contagion, as determined by external agents such as lawmakers, healthcare regulators or medical societies.

Embodiments of the invention may be used for identifying diagnostic and therapeutic options for medical conditions, based on information in electronic health records. Embodiments of the invention may be used to achieve final, definitive diagnoses or treatments. Further, embodiments of the invention may also or alternatively be used to generate outputs that are advisory rather than definitive or proscriptive. There are longstanding ethical, regulatory, legal and financial considerations that may make it important to generate outputs that are advisory rather than definitive or proscriptive. Some of these are discussed in the draft guidance document from the US FDA entitled Software as a Medical Device (SAMD): Clinical Evaluation, released Aug. 5, 2016 (http://www.fda.gov/downloads/MedicalDevices/DeviceRegulationandGuidance/GuidanceDocuments/UCM524904.pdf). In other words, embodiments of the invention do not necessarily constitute the practice of medicine nor do they necessarily contain expert knowledge, procedures or algorithms that might be erroneous or obsolete. Rather, the electronic health record database and outputs resulting from execution of above-described methods reflect statistical trends that have been observed in patients being diagnosed and treated by all physicians as available in the electronic health records that are compiled into the electronic health record database.

Because the underlying Bayesian methods associate actions with entities and outcomes that were actually observed, they may automatically identify practices that are useful rather than simply common. More specifically, through many instances of a physician performing actions on a patient as previously described, and recording the results and final diagnosis in the electronic health record database, this information becomes available to above-described methods. This allows above-described methods to adapt to advancements in medical technology and stay current with common or best practices. Such automatic adaptation is unlike hand-crafted algorithms based on the best practices of expert physicians, artificial intelligence algorithms that extract expert knowledge from medical journal articles, or diagnostic systems that attempt to apply systems models of physiology to make inferences about the condition of organs from diagnostic information, which are highly limited by their incomplete knowledge and also fail when facing complex interactions, especially in patients with more than one concurrent pathological condition. Further, because Bayesian inference is based on probabilities rather than logical rules, it deals well with the inevitable noise that contaminates a database collected under poorly controlled conditions such as electronic health records.

Because the methods require no expert knowledge or models besides the information in the database, the results of these algorithms may automatically reflect the current totality of all clinical experience in the database, which is constantly growing. It does not matter if the procedures and decisions of the practitioners that are captured in the database are frequently inefficient or erroneous, as long as the final diagnoses, whenever or however determined, are generally accurate or at least accepted by the medical community as reflective of the current standard of practice. Embodiments of the invention may, thus, automatically incorporate new diagnostic, preventive and therapeutic procedures as they appear in the growing electronic health record database and weight them automatically according to the amount and quality of data available for them in the database as well as their actual utility. While the electronic health record database may initially have little or no information about the existence or outcome of new treatments, embodiments of the invention may automatically incorporate, into the electronic health records, new clinical data as may arise in the course of use of the described methods.

Bayesian exploration, unlike other methods that can be unduly influenced by erroneous or outlier data in sparse regions of the multidimensional space, is at least somewhat immune to the challenges associated with sparse data. Due to its iterative and probabilistic nature, it deals well with high-dimensional and sparse data of electronic health records from large populations of patients. Electronic health records are particularly prone to "the curse of dimensionality." Databases of such records include a very large and rapidly growing set of data types from the diverse diagnostic processes listed above. New diagnostic tests such as genotyping, proteomic and microbiomic analysis are starting to expand these data types exponentially. As a consequence of this high dimensionality, the electronic health record is described as "sparse," because there may not be a significant number or perhaps any individuals who happen to have many specific combinations of all of these attributes, no matter how many individuals are represented in the database.

Embodiments of the invention may further generalize beyond diagnostic activities to also cover prevention and treatment. By defining actions to include treatments and defining results to include changes in values associated with successful treatment, the same process of finding the most efficient way to diagnose a condition may be used to find the most efficient way to treat it. Once the condition to be treated has been diagnosed, the electronic health record database may be queried to find the action (i.e. treatment) that will most likely produce the results (i.e. outcome measures) that are consistent with the successfully treated condition according to the clinical experience recorded in the electronic health records. This definition may also allow a given action to function simultaneously as both a diagnostic procedure and as a treatment, consistent with the notion of a therapeutic trial as described above. By incorporating null terms such as the diagnosis of "well-patient" and the action of "schedule for a future well-patient check-up," the subject invention may be applied to a health maintenance relationship in which the patient is always engaged in an active relationship of preventive medicine. By selection of an appropriate discount factor (as described above) for the weighting of costs and benefits, our invention may be tuned to provide advice that is more appropriate to address immediate complaints or to optimize quality of life over longer timeframes.

Embodiments of the invention may further automatically adjust their outputs to reflect various actual and/or imputed costs associated with diagnostic and treatment procedures, which tend to vary locally and to change over time as well as to depend on the diagnoses themselves.

While embodiments of the invention are not necessarily intended to be proscriptive, physicians or clinics that routinely deviate from those implicit recommendations may be wasting healthcare resources, endangering the health of their patients, or acting on perceived or actual inadequacies in the database upon which our invention operates. Such routine deviations are easily detected by embodiments of the invention and may be used to trigger investigations to understand why they are occurring. Conversely, if and when actions that are uncommon in the electronic health record database are used successfully by at least some physicians to diagnose, treat or prevent disorders, the benefits of such actions may be computed by the benefit analysis engine of our system, which may cause such actions to appear and/or to rise higher in the list of actions presented to the physician by our system. Embodiments of the invention may thus be relied upon to improve the efficiency of healthcare.

Embodiments of the invention may also be suitable for patients that may wish to understand their symptoms and possible diagnoses and treatments and may have access to sophisticated diagnostic procedures such as blood and genetic testing and medical imaging through commercial services. Patients who are uninsured or who are attempting to treat themselves may benefit greatly from an understanding of the range of diagnostic and therapeutic options available to them and the relative costs of those options. In one business model, patients may be provided with access to the software, algorithms and database that comprise our invention at no cost, with revenue instead derived from advertisements for and referrals to commercial diagnostic and therapeutic services, as discussed above with reference to FIG. 9C. In the various embodiments and descriptions of our invention, the terms "patient" and "physician" describe roles rather than mutually exclusive entities. A given person may simultaneously function as a patient and as his/her physician. More generally, "physician" herein refers to one who prevents, diagnoses and/or treats disease, injury and/or disability rather than being limited to any particular profession, certification, degree, license or other formal recognition. The patient or any caregiver may use our invention in the role of "physician."

Embodiments of the invention may be particularly suitable to support "personalized medicine," by helping deciding which competing treatment is most likely to be safe, effective and efficient or affordable for a given patient. Developing the data to inform such decisions has generally required massive, well-controlled clinical trials at huge expense. Data from such trials may not generalize to other populations with different genetic distributions or different life-styles and they quickly become obsolete as new treatments and new genetic markers are developed. Embodiments of the invention enable the automatic incorporation, into the health record database, of such clinical data as they may arise in the course of use of the subject invention. Embodiments of the invention may automatically consider such new diagnostic and therapeutic procedures that come to appear in the electronic health record database regardless of the means by which they were incorporated. For example, if the results of a particular gene screening test correlate with the probability of a patient having a specific disease or responding to a specific treatment, then as data from this test accumulate in the electronic health record database, embodiments of the invention may automatically recognize the utility of this information by recommending that the test be performed or by considering its results when evaluating the probability of a given diagnosis or the utility of a treatment.

Figure 10:
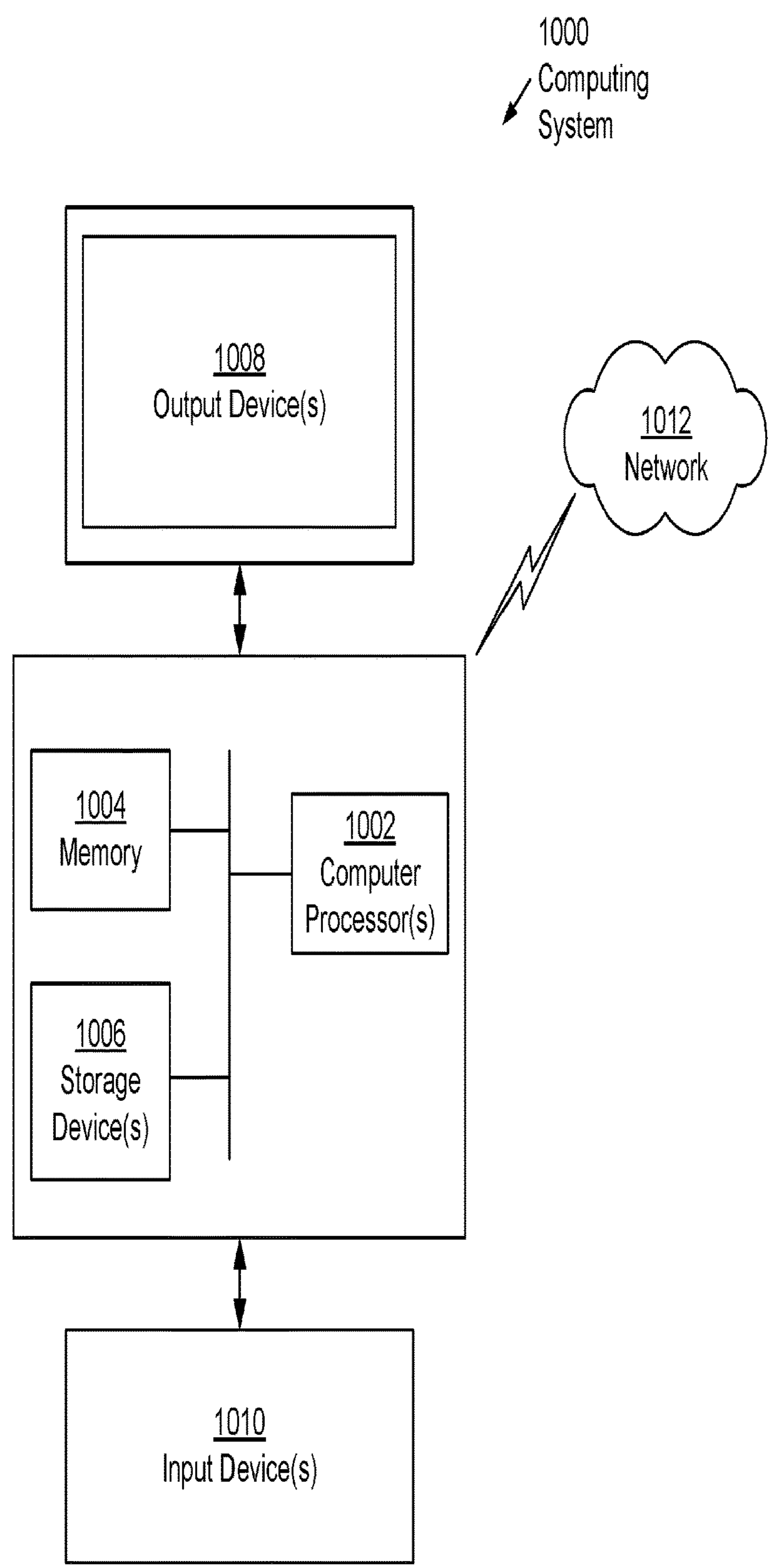
FIG. 10 shows a computing system, in accordance with one or more embodiments of the invention.

Embodiments of the technology may be implemented on a computing system. Any combination of mobile, desktop, server, embedded, or other types of hardware may be used. For example, as shown in FIG. 10, the computing system (1000) may include one or more computer processor(s) (1002), associated memory (1004) (e.g., random access memory (RAM), cache memory, flash memory, etc.), one or more storage device(s) (1006) (e.g., a hard disk, an optical drive such as a compact disk (CD) drive or digital versatile disk (DVD) drive, a flash memory stick, etc.), and numerous other elements and functionalities. The computer processor(s) (1002) may be an integrated circuit for processing instructions. For example, the computer processor(s) may be one or more cores, or micro-cores of a processor. The computing system (1000) may also include one or more input device(s) (1010), such as a touchscreen, keyboard, mouse, microphone, touchpad, electronic pen, or any other type of input device. Further, the computing system (1000) may include one or more output device(s) (1008), such as a screen (e.g., a liquid crystal display (LCD), a plasma display, touchscreen, cathode ray tube (CRT) monitor, projector, or other display device), a printer, external storage, or any other output device. One or more of the output device(s) may be the same or different from the input device(s). The computing system (1000) may be connected to a network (1012) (e.g., a local area network (LAN), a wide area network (WAN) such as the Internet, mobile network, or any other type of network) via a network interface connection (not shown). The input and output device(s) may be locally or remotely (e.g., via the network (1012)) connected to the computer processor(s) (1002), memory (1004), and storage device(s) (1006). Many different types of computing systems exist, and the aforementioned input and output device(s) may take other forms.

Software instructions in the form of computer readable program code to perform embodiments of the technology may be stored, in whole or in part, temporarily or permanently, on a non-transitory computer readable medium such as a CD, DVD, storage device, a diskette, a tape, flash memory, physical memory, or any other computer readable storage medium. Specifically, the software instructions may correspond to computer readable program code, that when executed by a processor(s), is configured to perform embodiments of the technology.

Further, one or more elements of the aforementioned computing system (1000) may be located at a remote location and connected to the other elements over a network (1012). Further, embodiments of the technology may be implemented on a distributed system having a plurality of nodes, where each portion of the technology may be located on a different node within the distributed system. In one embodiment of the technology, the node corresponds to a distinct computing device. Alternatively, the node may correspond to a computer processor with associated physical memory. The node may alternatively correspond to a computer processor or micro-core of a computer processor with shared memory and/or resources.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. A non-transitory computer-readable medium (CRM) comprising instructions that enable a system for identifying diagnostic options for medical conditions to:

obtain, from a plurality of electronic health records of previously examined patients, a plurality of diagnostic action results and a plurality of diagnoses, wherein the plurality of electronic health records is stored in an electronic health record database, wherein the plurality of diagnostic action results, stored in the electronic health record database, comprises quantifications of the plurality of diagnostic action results;

generate, for the plurality of diagnoses, a plurality of statistical distributions of the plurality of diagnostic action results, wherein at least one statistical distribution is generated for each of the plurality of diagnoses, and wherein the at least one statistical distribution is specific to one of the plurality of diagnostic action results;

establish a plurality of pairs of diagnoses from the plurality of diagnoses;

obtain a plurality of overlaps from the plurality of statistical distributions by:

for each of the plurality of pairs of diagnoses, quantifying an overlap of two statistical distributions of the diagnostic action results associated with one of the plurality of pairs of diagnoses;

obtain a plurality of benefits of the plurality of diagnostic action results by:

for each of the plurality of pairs of diagnoses, obtaining, based on the overlap of two statistical distributions of the diagnostic action results associated with one of the plurality of pairs of diagnoses, a benefit of the plurality of benefits of the diagnostic action results for disambiguating the pair of diagnoses, wherein the benefit positively correlates with an inverse of the overlap;

storing the plurality of benefits of the diagnostic action results in a diagnoses statistics database; and provide information to a user of the system regarding a patient to be diagnosed, using the plurality of benefits of the plurality of diagnostic action results stored in the diagnoses statistics database by:

obtaining an initial differential diagnosis for the patient to be diagnosed from an electronic health record of the patient to be diagnosed, wherein the initial differential diagnosis comprises a group of the plurality of diagnoses, the group selected to have a higher associated probability of correctly identifying a condition of the patient to be diagnosed than non-selected diagnoses of the plurality of diagnoses, based on the electronic health record of the patient to be diagnosed;

selecting a subset of the plurality of diagnostic action results for which the benefit is larger than for non-selected diagnostic action results of the plurality of diagnostic action results, to disambiguate the group of the plurality of diagnoses in the initial differential diagnosis; and providing a selection of diagnostic actions associated with the subset of the plurality of diagnostic action results to the user of the system.

2. The non-transitory CRM of claim 1, wherein the instructions further enable the system to:

obtain a cost for executing at least one of the selection of diagnostic actions.

3. The non-transitory CRM of claim 1, wherein the instructions further enable the system to:

provide the initial differential diagnosis to the user of the system; and provide, for each diagnosis in the group of the plurality of diagnoses, information about the associated probability of correctly identifying the condition of the patient to the user of the system, wherein the associated probability is provided by at least one selected from the group consisting of:

ordering the diagnoses in the group of the plurality of diagnoses according to the probability associated with each of the diagnoses, displaying the probability associated with each diagnosis in the group of the plurality of diagnoses, and identifying one diagnosis in the group of the plurality of diagnoses whose associated probability exceeds a conclusion threshold.

4. The non-transitory CRM of claim 1, wherein the instructions further enable the system to:

obtain a cost for executing at least one series of consecutive diagnostic actions, wherein each of the at least one series of consecutive diagnostic actions comprises at least one of the selection of diagnostic actions.

5. The non-transitory CRM of claim 4, wherein the instructions further enable the system to compute the cost, separately for executing each of the at least one series of consecutive diagnostic actions that reaches a conclusion threshold for a diagnosis in the group of the plurality of diagnoses.

6. The non-transitory CRM of claim 2, wherein the selection of diagnostic actions that are provided to the user of the system comprise diagnostic actions with a highest benefit to cost ratio, selected from the plurality of diagnostic actions, in comparison to non-selected diagnostic actions.

7. The non-transitory CRM of claim 1, wherein the instructions further enable the system to:

receive a new diagnostic action result obtained from performing a new diagnostic action on the patient to be diagnosed, update the electronic health record of the patient to be diagnosed by archiving the new diagnostic action and the new diagnostic action result; and obtain an updated differential diagnosis comprising an updated group of the plurality of diagnoses for the patient to be diagnosed.

8. The non-transitory CRM of claim 7, wherein the instructions further enable the system to:

conclude that at least one diagnosis in the updated group of the plurality of diagnoses matches the condition of the patient to be diagnosed, based on at least one selected from the group consisting of:

determining that a probability associated with the at least one diagnosis in the updated group of the plurality of diagnoses is above a conclusion threshold, and receiving, from the user of the system, a selection of the at least one diagnosis in the updated group of the plurality of diagnoses.

9. The non-transitory CRM of claim 8, wherein the instructions further enable the system to:

update the electronic health record of the patient to be diagnosed with the at least one diagnosis in the updated group of the plurality of diagnoses.

10. The non-transitory CRM of claim 7, wherein the instructions further enable the system to, after updating the electronic health record of the patient to be diagnosed:

update, in the diagnoses statistics database, the plurality of benefits of the plurality of diagnostic action results.

11. The non-transitory CRM of claim 1, wherein a plurality of confusion matrices is used to store the plurality of benefits of the plurality of diagnostic action results in the diagnoses statistics database, and wherein each confusion matrix of the plurality of confusion matrices is specific to one of the plurality of diagnostic action results.

12. The non-transitory CRM of claim 1, wherein obtaining the initial differential diagnosis for the patient to be diagnosed comprises eliminating diagnoses that have an associated probability below a consideration threshold from the group of the plurality of diagnoses.

13. A method for identifying diagnostic options for medical conditions, the method comprising:

obtaining, from a plurality of electronic health records of previously examined patients, a plurality of diagnostic action results and a plurality of diagnoses, wherein the plurality of electronic health records is stored in an electronic health record database, wherein the plurality of diagnostic action results, stored in the electronic health record database, comprises quantifications of the plurality of diagnostic action results;

generating, for the plurality of diagnoses, a plurality of statistical distributions of the plurality of diagnostic action results, wherein at least one statistical distribution is generated for each of the plurality of diagnoses, and wherein the at least one statistical distribution is specific to one of the plurality of diagnostic action results;

establishing a plurality of pairs of diagnoses from the plurality of diagnoses;

obtaining a plurality of overlaps from the plurality of statistical distributions by:

for each of the plurality of pairs of diagnoses, quantifying an overlap of two statistical distributions of the diagnostic action results associated with one of the plurality of pairs of diagnoses;

obtaining a plurality of benefits of the plurality of diagnostic action results by:

for each of the plurality of pairs of diagnoses, obtaining, based on the overlap of two statistical distributions of the diagnostic action results associated with one of the plurality of pairs of diagnoses, a benefit of the plurality of benefits of the diagnostic action results for disambiguating the pair of diagnoses, wherein the benefit positively correlates with an inverse of the overlap;

storing the plurality of benefits of the diagnostic action results in a diagnoses statistics database; and providing information to a user of the system regarding a patient to be diagnosed, using the plurality of benefits of the plurality of diagnostic action results stored in the diagnoses statistics database by:

obtaining an initial differential diagnosis for the patient to be diagnosed from an electronic health record of the patient to be diagnosed, wherein the initial differential diagnosis comprises a group of the plurality of diagnoses, the group selected to have a higher associated probability of correctly identifying a condition of the patient to be diagnosed than non-selected diagnoses of the plurality of diagnoses, based on the electronic health record of the patient to be diagnosed;

selecting a subset of the plurality of diagnostic action results for which the benefit is larger than for non-selected diagnostic action results of the plurality of diagnostic action results, to disambiguate the group of the plurality of diagnoses in the initial differential diagnosis; and providing a selection of diagnostic actions associated with the subset of the plurality of diagnostic action results to the user of the system.

14. The method of claim 13, further comprising:

obtaining a cost for executing at least one of the selection of diagnostic actions.

15. The method of claim 13, further comprising:

providing the initial differential diagnosis to the user of the system; and providing, for each diagnosis in the group of the plurality of diagnoses, information about the associated probability of correctly identifying the condition of the patient to the user of the system, wherein the associated probability is provided by at least one selected from the group consisting of:

ordering the diagnoses in the group of the plurality of diagnoses according to the probability associated with each of the diagnoses, displaying the probability associated with each diagnosis in the group of the plurality of diagnoses, and identifying one diagnosis in the group of the plurality of diagnoses whose associated probability exceeds a conclusion threshold.

16. The method of claim 13, further comprising:

obtaining a cost for executing at least one series of consecutive diagnostic actions, wherein each of the at least one series of consecutive diagnostic actions comprises at least one of the selection of diagnostic actions.

17. The method of claim 16, further comprising computing the cost, separately for executing each of the at least one series of consecutive diagnostic actions that reaches a conclusion threshold for a diagnosis in the group of the plurality of diagnoses.

18. The method of claim 14, wherein the selection of diagnostic actions that are provided to the user of the system comprise diagnostic actions with a highest benefit to cost ratio, selected from the plurality of diagnostic actions, in comparison with on-selected diagnostic actions.

19. The method of claim 13, further comprising:

receiving a new diagnostic action result obtained from performing a new diagnostic action on the patient to be diagnosed, updating the electronic health record of the patient to be diagnosed by archiving the new diagnostic action and the new diagnostic action result; and obtaining an updated differential diagnosis comprising an updated group of the plurality of diagnoses for the patient to be diagnosed.

20. The method of claim 19, further comprising:

concluding that at least one diagnosis in the updated group of the plurality of diagnoses matches the condition of the patient to be diagnosed, based on at least one selected from the group consisting of:

determining that a probability associated with the at least one diagnosis in the updated group of the plurality of diagnoses is above a conclusion threshold, and receiving, from the user of the system, a selection of the at least one diagnosis in the updated group of the plurality of diagnoses.

21. The method of claim 20, further comprising:

updating the electronic health record of the patient to be diagnosed with the at least one diagnosis in the updated group of the plurality of diagnoses.

22. The method of claim 19, further comprising, after updating the electronic health record of the patient to be diagnosed:

updating, in the diagnoses statistics database, the plurality of benefits of the plurality of diagnostic action results.

23. The method of claim 13, wherein a plurality of confusion matrices is used to store the plurality of benefits of the plurality of diagnostic action results in the diagnoses statistics database, and wherein each confusion matrix of the plurality of confusion matrices is specific to one of the plurality of diagnostic action results.

24. The method of claim 13, wherein obtaining the initial differential diagnosis for the patient to be diagnosed comprises eliminating diagnoses that have an associated probability below a consideration threshold from the group of the plurality of diagnoses.

25. The non-transitory CRM of claim 5, wherein the instructions further enable the system to:

select a first diagnostic action from the selection of diagnostic actions provided to the user of the system;

compute a plurality of sub-costs by:

for each diagnosis in the group of the plurality of diagnoses, compute a sub-cost to reach the conclusion threshold for that diagnosis when that diagnosis is the condition of the patient; and compute the cost of selecting the first diagnostic action as the probability weighted sum of the plurality of sub-costs to reach the conclusion threshold for all diagnoses in the group of the plurality of diagnoses.

26. The method of claim 17, further comprising:

selecting a first diagnostic action from the selection of diagnostic actions provided to the user of the system;

computing a plurality of sub-costs by:

for each diagnosis in the group of the plurality of diagnoses, computing a sub-cost to reach the conclusion threshold for that diagnosis when that diagnosis is the condition of the patient; and computing the cost of selecting the first diagnostic action as the probability weighted sum of the plurality of sub-costs to reach the conclusion threshold for all diagnoses in the group of the plurality of diagnoses.

* * * * *